(12) United States Patent
Neto

(10) Patent No.: US 8,969,030 B2
(45) Date of Patent: Mar. 3, 2015

(54) PROCESS TO PRODUCE BIODIESEL AND/OR FUEL OIL

(75) Inventor: Dolivar Coraucci Neto, Sertaozinho (BR)

(73) Assignee: Ouro Fino Participacoes e Empreendimentos Ltda, Alto da Boa Vista (BR)

(*) Notice: Subject to any disclaimer, the term of this patent is extended or adjusted under 35 U.S.C. 154(b) by 1204 days.

(21) Appl. No.: 12/521,848

(22) PCT Filed: May 2, 2008

(86) PCT No.: PCT/BR2008/000128
§ 371 (c)(1),
(2), (4) Date: Aug. 25, 2010

(87) PCT Pub. No.: WO2008/134836
PCT Pub. Date: Nov. 13, 2008

(65) Prior Publication Data
US 2010/0330615 A1  Dec. 30, 2010

(30) Foreign Application Priority Data

May 2, 2007 (BR) ........................... 0706170

(51) Int. Cl.
*C11B 1/00* (2006.01)
*C12P 7/64* (2006.01)
(Continued)

(52) U.S. Cl.
CPC .......... *C12P 7/649* (2013.01); *C10G 2300/1011* (2013.01); *C11B 1/10* (2013.01); *C11C 3/003* (2013.01); *C12N 1/22* (2013.01); *Y02E 50/13* (2013.01); *C10G 2300/1014* (2013.01)
USPC ................. 435/41; 435/42; 435/166

(58) Field of Classification Search
None
See application file for complete search history.

(56) References Cited

U.S. PATENT DOCUMENTS 2,625,474 A * 1/1953 Atkinson, Jr. et al. ........... 162/25
4,485,172 A * 11/1984 Gierhart ........................ 435/134

FOREIGN PATENT DOCUMENTS

| BR | 200406347 A | * | 7/2006 |
| BR | 200700179 A | * | 9/2008 |
| WO | WO 2008083453 A1 | * | 7/2008 |

OTHER PUBLICATIONS

UniProt "Taxonomy: Species *Rhodosporidium toruloides* (Yeast) (*Rhodotorula gracilis*)" UniProt Consortium, Taxonomy No. 5286, retrieved online Sep. 11, 2012 <url:http://www.uniprot.org/taxonomy/5286>, 1 page, 2012.*

(Continued)

*Primary Examiner* — Jon P Weber
*Assistant Examiner* — Aaron J Kosar
(74) *Attorney, Agent, or Firm* — Laurence P. Colton; Smith Risley Tempel Santos LLC

(57) ABSTRACT

The present invention refers to a process to produce biodiesel and/or fuel oil from microbial oilseed and/or algal biomass and/or from sugar cane residues and derivatives. The products according to the present invention are appropriate for direct use in motors and to generate energy or steam. The integrated process of the present invention comprises the use, as raw materials, of microbial oil-producing biomass obtained from sugar cane residues and derivatives, which is integrated with algal biomass and/or glycerol and are processed by steps of production of oil-producing microbial biomass from filamentous fungi and/or yeasts, steps of simultaneous production of algal biomass by fully using residues, $CO_2$ and residual broth of said production of microbial biomass, as well as steps of extraction and transesterification of lipids contained in the biomass, with reuse of the residual glycerol thus produced. The process as disclosed deals with innovative and ecologically sustainable technology, not generating any kind of residue, also providing for the advantage of releasing considerable volumes of oxygen into the atmosphere.

16 Claims, 7 Drawing Sheets

(51) Int. Cl.
  *C12P 39/00* (2006.01)
  *C11B 1/10* (2006.01)
  *C11C 3/00* (2006.01)
  *C12N 1/22* (2006.01)

(56) References Cited

OTHER PUBLICATIONS

Sheehan, et al "A Look Back at the U.S. Department of Energy's Aquatic Species Program: Biodiesel from Algae" Close-Out Report of the National Renewable Energy Laboratory (NREL), Jul. 1998, 328 pages.*

Kennedy, Max J.; Prapulla.S.G; Thakur,M.S. "Designing Fermentation Media: A Comparison of Neural Networks to Factorial Design" Biotechnology Techniques, 1992, 6(4), pp. 293-298.*

Singer, Emily "A Better Biofuel" Technology Review, Apr. 3, 2007, 4 pages.*

Wald, M.L. and Barrionuevo, A. "The Energy Challenge: A renewed Push for Ethanol, Without the Corn" NY Times Apr. 17, 2007, 4 pages.*

De la Hoz Siegler, Hector "Optimization of Biomass and Lipid Production in Heterotrophic Microalgal Cultures", Dissertation Univ. of Alberta, 2012, 332 pages.*

Xu, H. et al "High Quality Biodiesel Production from a Microalga *Chlorella protothecoides* by Heterotrophic Growth in Fermenters" J. Biotechnol., 2006,126 (4), pp. 499-507.*

Scott, SA; Davey, MP, Dennis, JS; Horst, I; Howe, CJ; Lea-Smith, DJ, Smith AG "Biodiesel from algae: challenges and prospects" Curr. Opin. Biotechnol., Apr. 17, 2010,21,pp. 277-286.*

Miao, X and Wu, Q "Biodiesel Production from Heterotrophic Microalgal Oil" Bioresource Technology, 2006 (online Jun. 4, 2005), 97, pp. 841-846.*

* cited by examiner

PROCESS TO PRODUCE BIODIESEL AND/OR FUEL OIL

FIELD OF THE INVENTION

The present invention refers to a process to produce biodiesel and/or fuel oil from microbial and/or algal oil-producing biomass and/or from sugar cane residues and derivatives. The products according to the present invention are appropriate for direct use in motors and to generate energy or steam.

BACKGROUND OF THE INVENTION

Considering current forecasts that petroleum sources will be exhausted within the next decades, other energy sources have been researched worldwide. Among these alternatives, biofuels, such as ethanol and biodiesel, present a significant potential, since they are low pollutant and also renewable energy forms.

In the specific case of biodiesel, for large scale production, technologies have been developed from raw materials rich in lipids and fatty acids of plant and animal origin. Unfortunately, lipids and fats derived from plants and animals as produced worldwide only meet the demand for the consumption for food production and oleochemical industries. Therefore, it is extremely important to search for other alternative sources for the production of lipids and fatty acids for use in the production of biodiesel and fuel oil. The microbial synthesis of lipids and fats is a technological alternative for this purpose.

There are three main advantages in lipid production by microorganisms. First, generation is very quick, i.e. the microbial biomass doubles in an interval of hours, yeasts produce a new generation between one and three hours, algae between two and six hours and fungi between four and twelve hours. Second, less production area is required for one single mass of fat material, i.e. it is possible to produce in a fermentor the same quantity of lipids in much less time and in an area up to thirty times smaller than used to plant vegetables. And third, it is possible to better control the production process and the product, i.e. bioreactor, or fermentor, control is much simpler than the control of agricultural production, besides not depending on climate and/or season variations.

Not all microorganisms accumulate lipids in enough quantity to make their economic and industrial production become viable. Microorganisms considered as oil producers are those that can accumulate more than 20% lipids within their dry biomass. Basics of physiology to accumulate lipids by microorganisms have been studied by various researchers worldwide.

Yeasts may be mentioned as one of the most interesting groups of microorganisms, for their ability to accumulate large quantities of lipids intracellularly, as well as for their relatively high rates of growth and their similarity in triglyceride composition with vegetal oils.

In some cases, said microorganisms may accumulate up to 70% of their dry weight in lipids, and the main formed triglycerides have chains between 16 and 18 atoms of carbon.

During the Second World War, due to scarce vegetal lipids, the cultivation of yeasts enabled the manufacture of oils and their derivatives, such as margarines and other products. In the current cosmetic industry, fatty acids with high commercial value are used as emulsifiers and stabilizers. Said lipids may equally be synthesized by microbial route.

Algae represent another important source of lipids and are equally able to accumulate concentrations of up to 65% over the weight of their dry biomass. They may be classified as photosynthetic organisms, such as plants, since they use solar energy, jointly with water and carbon dioxide, to generate biomass. Within said classification, the present invention also has the purpose to make use of photosynthetic organisms growing in water environment, i.e. macroalgae, microalgae and other water organisms for the production of commercially interesting products, particularly lipids for the production of biodiesel and fuel oil.

Macroalgae are quickly growing plants reaching considerable sizes, about 50 m long. On the other hand, microalgae, as their name suggests, are microscopic photosynthetic organisms found in marine and fresh water environments.

The study of microalgae is still relatively unknown and algae as a whole still are a very little understood and used organism, biotechnologically speaking. Microalgae are divided into a series of classes, according to their pigments, life cycle and basic cell structure. The four most important classes of microalgae in terms of abundance are Bacillariophyceae, Chlorophyceae, Cyanophyceae and Chrysophyceae. They are the most primitive forms of plants, have similar photosynthetic mechanisms to higher plants, but convert solar energy into more efficient forms, due to their simple cell structure. Furthermore, since cells grow in water suspension, they have more access to water, carbon dioxide and other nutrients. For these reasons, microalgae are able to produce thirty or more times the quantity of oil per unit of planted area, in comparison to oilseeds.

We can state, therefore, that microalgae form a heterogeneous group, including photosynthesizer microorganisms, both eukaryotic and prokaryotic. Microalgae are usually unicell, gram-negative and predominantly live in water environment.

The high photosynthetic efficiency of said microorganisms make them form the base of the food chain in water ecosystems, being responsible for about 40-50% carbon fixing and oxygen production on the planet. Furthermore, microalgae synthesize organic matter from inorganic substances, such as salts, carbon dioxide and water.

From that knowledge, the microbial production of lipids appears as a viable and innovative alternative in the competition with the production of vegetal and/or animal oils and fats. Microorganisms, as simpler living beings than plants and animals, may be economically used in large or small scale for the production of biodiesel or to generate energetic fuels, as well as to generate other products.

BRIEF DESCRIPTION OF THE INVENTION

It is therefore an object of the present invention to provide an industrial process to integrate various sources of raw material for the production of biodiesel and/or fuel oil, as a considerable alternative to current fossil fuels.

Products, oils with microbial and/or algal origin, object of the present invention, are non-pollutant and obtained from renewable sources, comprising sugar cane derivatives and residues, such as juice, molasses, white and/or full sugar, sugars produced by the hydrolysis of leaves and/or bagasse, residual liquid effluents from the production of microbial biomass and carbon dioxide, besides glycerol, a subproduct from biodiesel production. All these substrates may be used isolated or integrated in any form into one single innovative and environmentally friendly process.

Illustrative figures as attached detail the characteristics of the process to produce biodiesel and/or fuel oil of the present invention, in which.

DETAILED DESCRIPTION OF THE INVENTION

Figure 1:
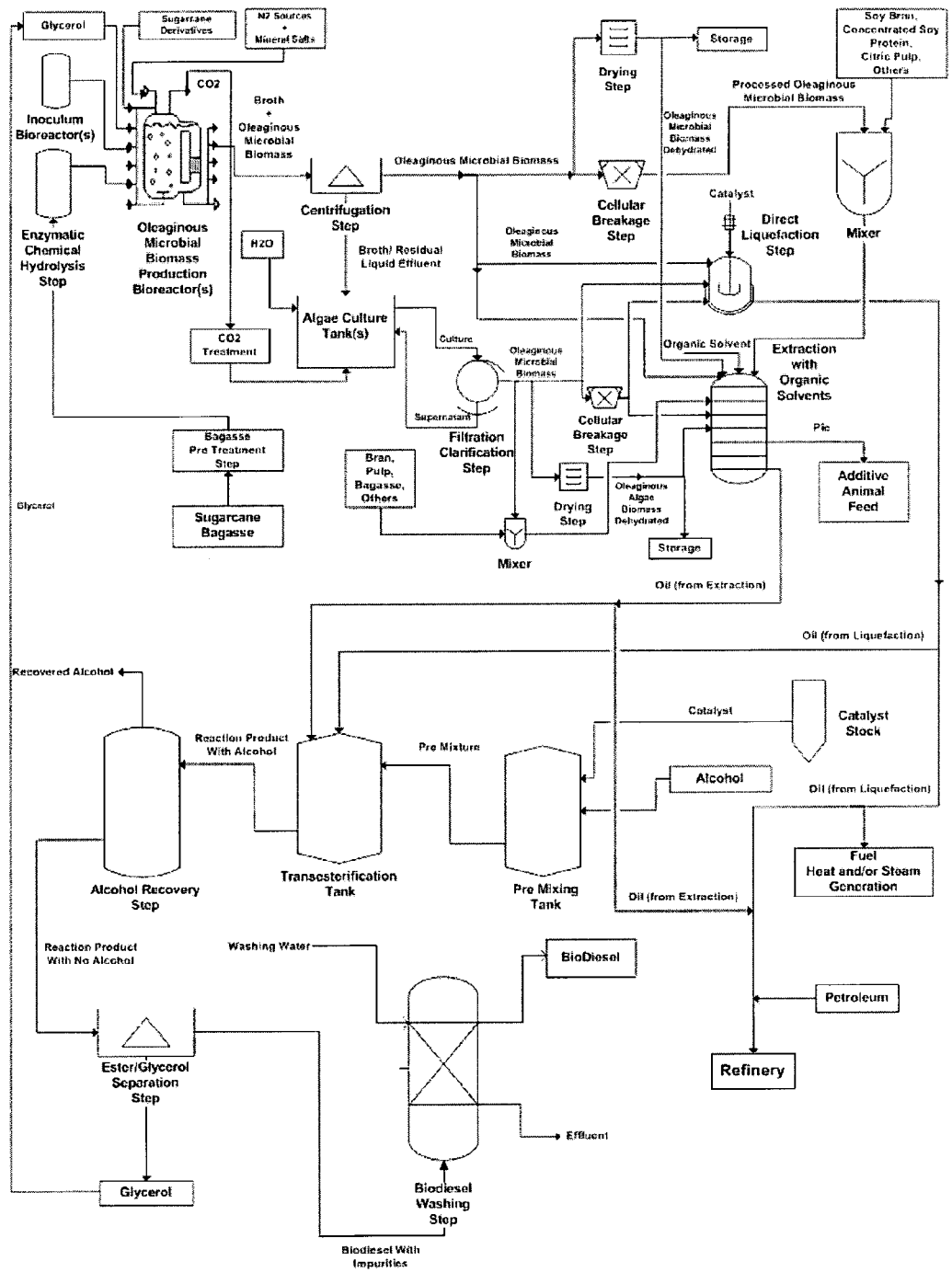
FIG. 1 shows a general flow chart of the integrated process of the present invention.

As shown by FIG. 1, according to the present invention, the process to produce biodiesel and/or fuel oil from microbial and/or algal oil-producing biomass obtained from sugar cane residues and derivatives, as integrated, comprises seven processing units, which cover the steps of production and extraction of algal and microbial lipids, the step to produce oil-producing microbial biomass from filamentous fungi and/or yeasts as obtained from sugar cane derivatives and residues, as well as the step of biodiesel production and re-use of glycerol originating from the lipid transesterification unit. Algal biomass is simultaneously produced by the full use of residues, $CO_2$ and residual juice, liquid effluent from the production of microbial biomass. Said basic units comprise:

a set of Sugar Cane Bagasse Processing (Unit 1);

A set of Microbial Biomass Production from Sugar Cane Derivatives, Hydrolysed Sugar Cane Bagasse and Glycerol (Unit 2);

a set of Oil-producing Microbial Biomass Processing (Unit 3);

a set of Algal Biomass Cultivation and Recovery (Unit 4);

A set of Direct Thermal Extraction and Liquefaction of Microbial and/or Algal Lipids (Unit 5);

A set of Lipid Transesterification (Unit 6); and

A set of Processing for Use of Fuel Oil as Obtained by Direct Thermopressurized Liquefaction to Generate Heat and/or Steam and Application as an Adjuvant to Petroleum (Unit 7).

The process of the present invention will be disclosed below by the operational sequence of processing of various sources of raw materials to produce biodiesel and/or fuel oil. Processing as disclosed was made in study and analysis facilities under lab conditions. Therefore, the various steps of the process of the invention comprise:

1$^{st}$ Step—Acid Hydrolysis of Sugar Cane Bagasse

Figure 2:
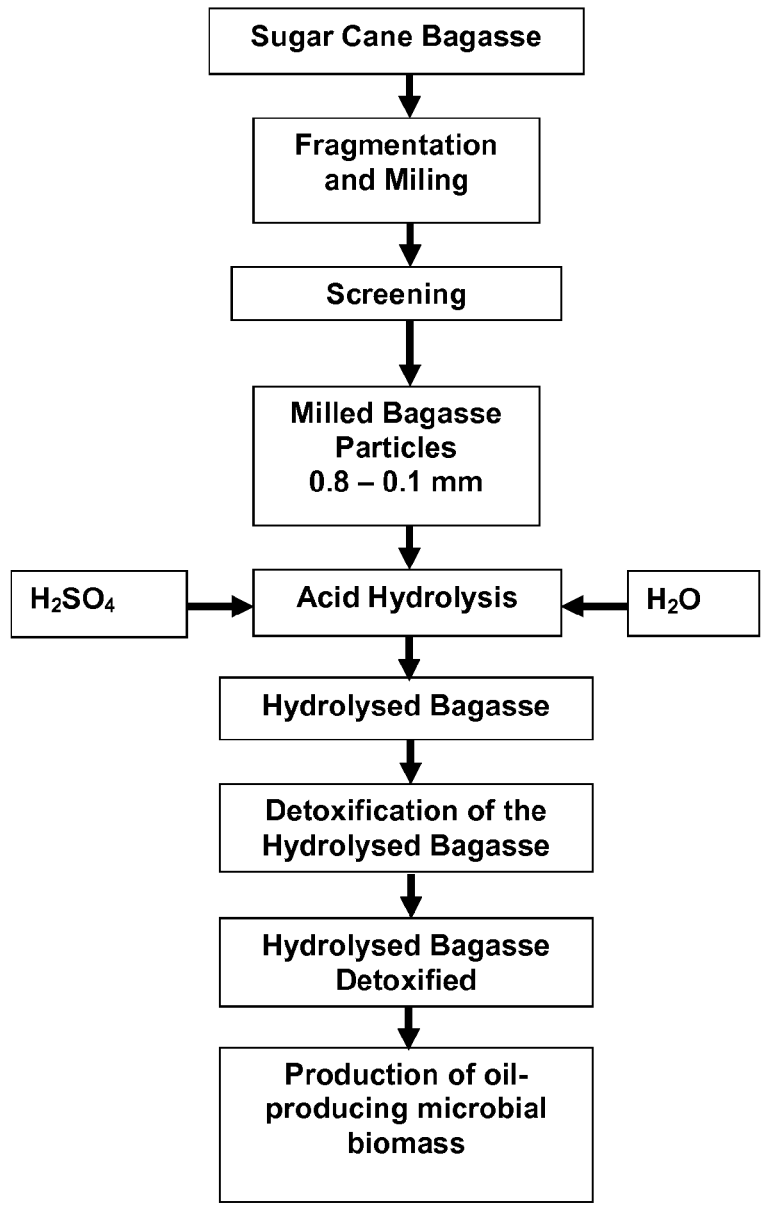
FIG. 2 shows a flow chart of the steps of pre-treatment and hydrolysis of sugar cane bagasse.

In Unit 1—Processing of Sugar Cane Bagasse, as shown by the flow chart of FIG. 2, the sugar cane bagasse resulting from juice extraction, which is a lignocellulose residue produced in large volumes, average 150 kg/ton of milled cane, is reused after hydrolysis as a source of carbon in the production process of oil-producing microbial biomass from filamentous fungi and/or yeasts. With that purpose, sugar cane bagasse passes through two basic fundamental steps, pre-treatment and hydrolysis.

Pre-Treatment of Sugar Cane Bagasse

Pre-treatment of sugar cane bagasse is required to change the size and structure of lignocellulose fibers, both micro and macroscopically, as well as to change their chemical composition and submicroscopic structure, so that the hydrolysis of the carbohydrate fraction in monomeric sugars may be reached more quickly and under higher yielding. The objects of pre-treatment are to remove lignin and hemicellulose, to reduce cellulose crystallinity and to increase the porosity of materials. Good pre-treatment improves the formation of sugars or the ability of their formation by enzymatic hydrolysis, also avoiding the degradation or loss of carbohydrates and the formation of subproducts which may inhibit subsequent hydrolysis reactions and the formation of oil-producing microbial biomass. Pre-treatment as used by the process of the present invention may be effected by physical means, such as mechanical grinding or milling, or by physical-chemical, chemical, biological means or their combinations.

According to the present invention, physical pre-treatment means are preferred, most preferably mechanical grinding, which is a combination of cutting, fragmentation and milling of bagasse. Dry sugar cane bagasse is milled in a knife grinder, such as trademark Sadrind K8/25. Subsequently, said material is screened, and the fraction containing 0.1-0.8 mm particles is sent to the acid hydrolysis step. For mechanical grinding, other types of equipments may be equally used, such as vibrating basket mills, ball mills, hammer grinders, roll grinders, kneaders or any other equipment always aiming to reduce sugar cane bagasse, leaves and cutting particles to facilitate the hydrolysis of said cellulose material.

Among physical-chemical pre-treatments which may be equally used for the process of the present invention, we refer to steam explosion, ammonia fiber explosion and $CO_2$ explosion. In steam explosion, sugar cane bagasse should be initially milled, treated with high pressure saturated steam and submitted to abrupt pressure reduction. Said procedure usually occurs between 100 and 300° C. and 0.43-5.57 MPa, during a period of time from a few seconds to various minutes.

Similarly, in the pre-treatment with ammonia, sugar cane bagasse is exposed to liquid ammonia under high temperature and high pressure, followed by abrupt temperature drop. This procedure uses about 1-2 kg of liquid ammonia/kg of dry sugar cane bagasse at a temperature between 60 and 120° C. for a reaction period between 10 and 60 minutes.

In the case of $CO_2$ explosion, however, about 2-5 kg of $CO_2$/kg of sugar cane bagasse are used, pressures are about 5.62 MPa for a similar time period to the other two techniques.

Furthermore, according to the present invention, chemical pre-treatment of sugar cane bagasse can be made by ozonolysis, acid hydrolysis, alkaline hydrolysis and alkaline delignification, among others.

Ozonolysis consists in degradation of lignin and hemicellulose by using ozone. Ozonolysis is preferred for being more advantageous, since it does not produce toxic residues, reactions occur at room temperature and it removes lignin much efficiently. Chemical pre-treatment by acid route may use, among others, diluted or concentrated sulfuric acid, hydrochloric acid and phosphoric acid, under critical pressure and temperature conditions or not and continuously or in batches. Said technique, however, requires a neutralization step for the material to be used for the production of oil-producing microbial biomass. On the other hand, chemical pre-treatment by alkaline route has the same variants of acid hydrolysis, but using sodium hydroxide, ammonia or other alkaline compounds under concentrations varying between 2 and 30%.

Besides these three chemical methods as mentioned herein, there is also the possibility to effect oxidative delignification of sugar cane bagasse by means of its exposure to hydrogen peroxide under 1 to 5% concentrations and temperatures between 20 and 50° C. for a time period of five to thirty minutes.

There is also the possibility to pre-treat sugar cane bagasse by means of biological procedures. For that purpose, microorganisms, such as basidiomycetes fungi (brown, white and soft-rot fungi), able to degrade lignin and hemicellulose, are used.

All pre-treatments of sugar cane bagasse as mentioned above are incorporated to the object of the present invention.

Following pre-treatment, sugar cane bagasse is hydrolysed, and carbohydrate polymers are thus converted into monomeric sugars. Cellulose may hydrolytically disrupt glucose both enzymatically, by the action of cellulases, and chemically, by the action of acids. After hydrolysis, six-carbon sugars, also called hexoses (glucose, galactose and mannose) are promptly fermented, while pentoses (xilose and arabinose) are fermented just for a few microorganism lines or strains. Chemical hydrolysis may be effected by the use of diluted or concentrated acid, such as sulfuric acid, hydrochloric acid, phosphoric acid and/or other acids, with concentrations between 2 and 80%, to temperatures varying between 25 and 150° C. for a reaction period varying from a few minutes to various hours, with or without acid recovery or neutralization systems.

Also, according to the present invention, enzymatic hydrolysis of sugar cane bagasse is made by using highly specific enzymes, known as cellulases. Said method uses much softer conditions in comparison with acid hydrolysis, occurring under pH ranges around 4.5 and temperatures between 25 and 60° C. Cellulases are usually a mixture of various enzymes and, in the process of the present invention, we prefer the use of endoglucanases (EC 3.2.1.4), exoglucanases (EC 3.2.1.91) and/or β-glucosidases (EC 3.2.1.21). According to the present invention, hydrolysis may be effected with concentrated or non-concentrated substrates, under cellulase concentrations between 5 and 40 FPU/g of substrate, time of reaction between 24 and 96 hours and using immobilized or non-immobilized enzymes.

Since it is considered as more advantageous and economic, acid hydrolysis is preferred, according to practical results as obtained under optimized conditions.

Acid Hydrolysis of Sugar Cane Bagasse

As shown by FIG. 2, dry and milled sugar cane bagasse with particles between 0.1 and 0.8 mm is hydrolysed in a stainless steel reactor AISI 316 with 10 liter capacity at 125° C. for twenty minutes, using 1 kg of dry matter for 120 grams of concentrated $H_2SO_4$ with solid-liquid ratio of 1:10.

After hydrolysis, the suspension is spinned to remove non-hydrolysed solid residues, which are washed with water to extract remaining sugars. Hydrolysate (supernatant) as obtained is concentrated about six times in a vacuum rotatory evaporator such as the dryer BÜCHI R-215, at a temperature of about 65° C., as a form to increase the full sugar concentration as present in the hydrolysate. The concentrated hydrolysate is then treated to eliminate toxic compounds derived from furane, such as furfural and hydroxymethylfurfural, derived from lignin degradation, which are phenolic compounds, and weak acids such as acetic acid, formic acid and levulinic acid, which are formed during the acid hydrolysis process and act as substances inhibiting microbial growth, in this case yeasts. The hydrolysate of sugar cane bagasse is finally detoxified as per the technique disclosed by Marton et al (2003), consisting in changing pH by adding commercial calcium oxide (CaO) up to pH 7.0, followed by acidification with phosphoric acid up to pH 2.5 and later neutralization with calcium oxide (CaO). In each one of said pH change steps, precipitate is removed by filtration. Subsequently, hydrolysate is mixed with granular activated carbon at a rate of 10 grams of carbon for each 1 liter of hydrolysate in a stainless steel reactor AISI 316, with ten liter capacity, containing within it a mechanical shaking system by blades. The best results in terms of detoxification of hydrolysate of sugar cane bagasse were reached after treatment for a time of about forty minutes, under temperatures of about 65° C. and with shaking of about 245 rpm.

Sugars (glucose, xylose and arabinose) and the acetic acid as present in the concentrated hydrolysate were identified and quantified in a high performance liquid chromatograph (HPLC) trademark Shimadzu model LC-10 AD, refraction rate detector in an AMINEX HPX-87H column by Bio-Rad, using 5 mM $H_2SO_4$ as the mobile phase, 60° C. as the temperature of the refraction rate detector oven. Samples were spinned at 4500 rpm for 15 minutes, diluted with ultrapure water and filtered through cellulose ester membrane with porosity of 0.22 μm. Total phenol concentration was made by the method of Singleton et al (1999), using reagent Folin Ciocalteau. Table 1 shows the chemical composition of sugar cane bagasse hydrolysate after detoxification treatment by using activated vegetal carbon and pH change. Xylose is the main carbohydrate, representing approximately 87% of sugars as present in concentrated and detoxified sugar cane bagasse hydrolysate. Pre-treatment for detoxification of sugar cane bagasse hydrolysate reduced in about 17.41% the concentration of xylose over its initial value. In the case of toxic phenolic compounds, this reduction was about 88.85%, but in the case of acetic acid, it was about 63.73%.

TABLE 1

CHEMICAL COMPOSITION OF 6X CONCENTRATED SUGAR CANE BAGASSE HYDROLYSATE

| Components | Hydrolysate (g/l) 6X Concentrate | |
| --- | --- | --- |
| | 1 | 2 |
| Glucose | 6.12 | 5.53 |
| Xylose | 108 | 89.28 |
| Arabinose | 8.90 | 8.10 |
| Acetic acid | 5.10 | 1.85 |
| Phenols | 8.52 | 0.95 |
| pH | 7.0 | 7.0 |

Figure 3:
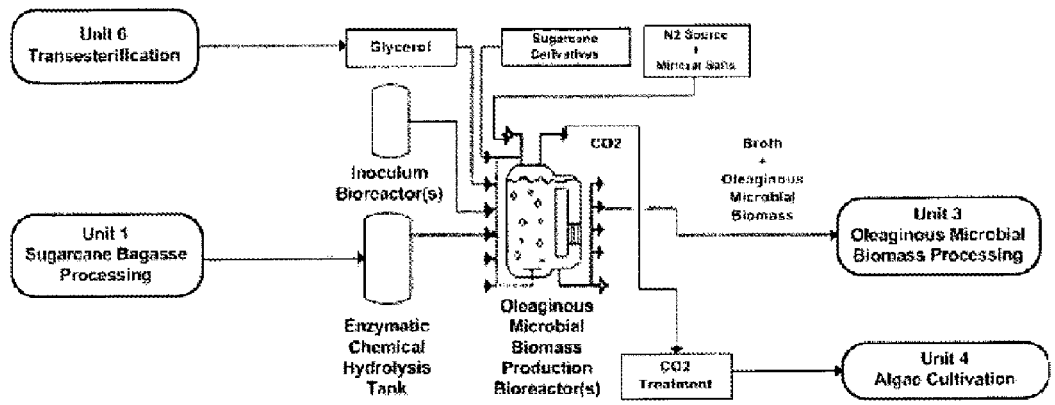
FIG. 3 shows a flow chart of the unit of production of oil-producing microbial biomass.

1 = before detoxification; 2 = after detoxification $2^{nd}$ Step—Production of Microbial Biomass from Oil-Producing Yeast In Unit 2—Production of Microbial Biomass, as shown by FIG. 3, basic raw materials as used are sugar cane derivatives, such as juice, molasses, brown and/or white sugar, concentrated and detoxified hydrolysed sugar cane bagasse (BHCD), glycerol and/or their mixtures. In this step, according to the present invention, we make:

Isolation and Identification of the Yeast Strain

The oil-producing yeast *Rhodosporidium toruloides* OF A25 was isolated from soil in a sugar cane plantation in the State of Parana—Brazil and identified for its morphological characteristics and physiological properties, biochemical metabolism as by molecular biology techniques. The strain *R. toruloides* OF A25 has been selected for its ability to accumulate triacylglycerol (TAG) in its biomass when cultivated in media rich in sources of carbon, such as sucrose and xylose, derived from molasses, sugar cane bagasse hydrolysate and glycerol, but poor in sources of nitrogen. The strain *R. toruloides* OF A25 was conserved by lyophilization in freezer, under temperature of about 80° C. and subcultivated on broth and agar YM.

Growth of *R. toruloides* of A25 on Different Sources of Carbon

This experiment was based on the use of different residues originating from sugar cane industrialization. Sugar cane molasses (MCA) is a dark viscous liquor, rich in non crystallizable sugars, generated during sugar manufacture. Its composition is very variable, since it depends on agricultural and industrial factors such as the variety of sugar cane, its maturation grade and weather conditions, among others. Main components of molasses are water, carbohydrates and compounds with organic origin such as aminoacids, aliphatic and olephinic carboxillic acids, vitamins, proteins and phenols, among others. Molasses also contain a fraction of mineral origin with high significance, in which metals and non-metals are present under significant proportions. Table 2 below presents the average composition of sugar cane molasses as used in the process of the invention as disclosed herewithin, which was purchased from the company Jardest S. A. Açúcar e Álcool, Via Ánhangüera km 340—Jardinopolis—SP, Brazil. Sucrose is the predominant sugar and represents about 80% of present sugars. The present invention also refers to the use of sugar cane juice in which, although sucrose appears as the predominant sugar, its concentration is lower than found in molasses.

TABLE 2

PHYSICAL/CHEMICAL COMPOSITION OF SUGAR CANE MOLASSES

| Component | % |
|---|---|
| Sucrose | 46.9 |
| Glucose | 5.2 |
| Fructose | 6.7 |
| Ashes | 11.5 |
| Other non-carbohydrate substances | 16.4 |
| Water | 14.5 |
| pH | 5.5 |

As already reported, the present invention refers to the use of isolated glycerol and/or in association with sugar cane molasses and/or juice and/or bagasse hydrolysate as a source of carbon for the production of oil-producing biomass of *Rhodosporidium toruloides* OF A25. Glycerol constitutes a subproduct, residue from the lipid transesterification process, in this case triacylglycerols (TAG), during the manufacture of biodiesel from algal and/or oil-producing yeast biomass. Integrated recycling of all these residues is a major factor for the objects of the present invention.

Preparation of Inoculation

To prepare the inoculation, the strain *Rhodosporidium toruloides* OF A25 was defrozen, fragmented over solid YM (Yeast Medium) media an submitted to growth in a oven at about 30° C. for five days. It was delivered in a laminar flow chamber to 500 ml Erlenmeyer flasks containing 100 ml of sterile YM liquid medium. These flasks were transported to a rotating movement incubator New Brunswick Scientific Co. at about 30° C., 150 rpm for a period of about 72 hours. The liquid YM medium is composed by glucose (10 g/l), peptone (5.0 g/l), yeast extract (3.0 g/l), malt extract (3.0 g/l), Agar (20 g/l) and at pH 5.0. The only difference between this medium and solid YM is the presence of Agar under concentration of 20 g/l.

Production of Biomass from Oil-Producing Yeast *Rhodosporidium toruloides* of A25

Two-liter Erlenmyer flasks containing 400 ml of different sterile cultivation media, as shown by Table 3 (conditions 1 to 15) below, were inoculated with 10% v/v active culture recently obtained from *Rhodosporidium toruloides* OF A25, as disclosed in the previous item, with pH adjusted to about 5.0 with 1.0 N HCl. Flasks were transported to a rotating movement incubator New Brunswick Scientific Co. at temperature of about 30° C., 150 rpm, for about 72 hours. As the source of carbon, sugar cane molasses were used (a substrate rich in sucrose), 6× concentrated detoxified sugar cane bagasse hydrolysate (substrate rich in xylose), glycerol (subproduct from biodiesel production) and their associations. According to an aspect of the present invention, sugar cane molasses may be perfectly substituted by sugar cane juice as a function of availability, seasonal availability and process savings. Concentration in terms of full sugar, present in sugar cane molasses and sugar cane bagasse hydrolysate, is determined by the sulfuric phenol method or in a high performance liquid chromatograph (HPLC) trademark Varian Pro Star, model 500, with solvent distribution module model 240, oven model 500, refraction rate detector model 350, software Workstation 5.0, separation column Shodex SZ 5532, separating components of samples by molecular size. Analysis conditions were in mobile phase $H_2O$:acetonitrile (20:80), 1 ml/min, 65° C., injection volume 15 μl (loop capacity 5 μl). Concentration reading standardization is made with water solutions of 1 to 20 g/l analytical grade standard. Samples are previously spinned (10,000 g, 5 min) and filtered through 0.22 μm hydrophilic PVDF membranes (Millipore). In case of glycerol, its concentrations in experiments were quantified by HPLC. All experiments have been made in triplicate. Two sources of nitrogen were selected and used, specifically yeast extract and urea, or their combinations and mixtures. We underline that other sources of nitrogen, with organic or inorganic origin, as well as varied concentrations may be used, with the object to maximize production and/or lipid accumulation in the microbial biomass of the present invention.

After cultivation for about 72 hours, flasks were taken from the incubator and the oil-producing biomass was separated by filtering in quantitative filter paper under vacuum. After first filtration, biomass was washed twice with distilled water, dried in a vacuum oven for about 24 hours at about 60° C. and weighed in analytical scales. Full lipid concentration as present in yeast biomass was determined by Soxhlet extraction.

TABLE 3

PRODUCTION OF BIOMASS AND LIPIDS BY *RHODOSPORIDIUM TORULOIDES* OF A25 IN DIFFERENT SOURCES OF CARBON AND NITROGEN

| A | B | C | D | E | F | G | H |
|---|---|---|---|---|---|---|---|
| 1 | — | — | 100 | 10 | — | 16.05 | 15.14 ± 0.97 |
| 2 | — | 100 | — | 10 | — | 18.73 | 24.30 ± 1.74 |
| 3 | 100 | — | — | 10 | — | 32.13 | 41.18 ± 1.42 |

TABLE 3-continued

PRODUCTION OF BIOMASS AND LIPIDS BY *RHODOSPORIDIUM TORULOIDES* OF A25 IN DIFFERENT SOURCES OF CARBON AND NITROGEN

| A | B | C | D | E | F | G | H |
|---|---|---|---|---|---|---|---|
| 4 | 100 | — | — | — | 2.5 | 27.60 | 31.03 ± 2.73 |
| 5 | — | 100 | — | — | 2.5 | 14.21 | 14.62 ± 0.94 |
| 6 | — | — | 100 | — | 2.5 | 12.65 | 9.25 ± 1.05 |
| 7 | 50 | 50 | — | 10 | — | 26.53 | 34.01 ± 1.12 |
| 8 | 50 | — | 50 | 10 | — | 22.08 | 29.05 ± 1.50 |
| 9 | — | 50 | 50 | 10 | — | 10.12 | 16.44 ± 1.35 |
| 10 | 50 | 50 | — | 5 | 1.25 | 24.44 | 30.10 ± 0.54 |
| 11 | — | 50 | 50 | 5 | 1.25 | 23.07 | 25.33 ± 2.04 |
| 12 | 40 | 30 | 30 | — | 2.5 | 15.49 | 17.02 ± 0.71 |
| 13 | 40 | 30 | 30 | 5 | 2.25 | 26.47 | 33.61 ± 2.13 |
| 14 | 30 | 40 | 30 | — | 2.5 | 8.15 | 13.12 ± 0.34 |
| 15 | 30 | 30 | 40 | — | 2.5 | 9.17 | 14.00 ± 1.11 |
| 16 | 30 | 30 | 40 | 5 | 2.5 | 19.25 | 24.79 ± 2.02 |

A = Condition of Culture
B = Cane Molasses (g/l)
C = 6X concentrated detoxified cane bagasse hydrolysate (g/l)
D = Glycerol (g/l)
E = Yeast extract (g/l)
F = Urea (g/l)
G = Biomass (g/l)
H = Lipids (%)

Results as shown by Table 3 above show that the yeast *Rhodosporidium toruloides* OF A25 may grow and accumulate high concentrations of lipids in media containing residues from the industrialization of sugar cane, such as molasses, juice and bagace hydrolysate, as well as glycerol, a residue generated during biodiesel manufacture. Condition of Culture 3 provided the best conditions for cell growth and lipid accumulation. As previously underlined, sugar cane molasses, besides being rich in sucrose, also contain aminoacids, olephinic and aliphatic carboxylic acids, vitamins, proteins and numerous minerals. Even when the source of nitrogen of organic origin (such as yeast extract) is substituted for another one of fossil origin (such as urea), the production of dry biomass was high, about 27.60 g/l, with lipid content of about 31.03%, as per Culture Condition 4. Said yeast also showed being able to grow and accumulate lipids when cultivated in concentrated and detoxified sugar cane bagasse hydrolysate (BHCD). As already mentioned, said hydrolysate is rich in xylose. With the presence of yeast extract in the medium containing BHCD, the concentration of dry biomass was about 18.73 g/l. When urea was used as a source of nitrogen said concentration was 14.21 g/l, lipid concentrations in dry biomass were respectively 24.30% and 14.62%, as per Culture Conditions 2 and 5. *Rhodosporidium toruloides* OF A25 also showed high efficacy in the assimilaton of glycerol when used as the only source of carbon in the culture medium. The production of dry biomass was about 16.05 and 12.65 g/l of dry biomass formed after 72 hours of culture in shaker, having accumulated respectively 15.14% and 9.25% lipids when the sources of nitrogen were yeast extract and urea, as shown by Culture Conditions 1 and 6.

Production of Biomass from Oil-Producing Yeast *Rhodosporidium toruloides* of A25 in a Bioreactor Different 20 ml aliquotes of medium X (inoculate) prepared as per the above disclosed methodology were transported to 2 l sterile Erlenmeyer flasks and mixed with 180 ml of sterile medium Y (adaptation). Said compositions are disclosed by Table 4 below. Said flasks were incubated in a rotating shaker at 30° C. for about 48 hours at 150 rpm. After this time, yeast is perfectly adapted and presents vigorous growth in the new medium. Said growth and adaptation of yeast to medium Y is evaluated by taking samples every six hours and counting viable cells, previously painted with 1% erythrosin in a Neubauer chamber. Bioreactor containing a vase of about 14 l was fulfilled with 9.0 l of the culture medium Z. The bioreactor vase was transported to an autoclave and the set vase+medium Z was sterilized at about 120° C. for fifteen minutes. After cooling at the temperature of 30° C., this medium was inoculated with 1 l of an active culture of about 48 hours of medium Y. Biomass production from oil-producing yeast in a bioreactor was conducted for about 72 hours in an equipment trademark New Brunswick Scientific, model Bioflo 110, total volume of 14 l, working volume of 10 l, $dO_2$ and pH control module with $O_2$ probe Mettler Toledo InPro 6800 Series $O_2$ Sensors and pH probe Mettler Toledo 425 mm model 405 DPAS-SC-K85/425 and two peristaltic pumps for the addition of acid or base, foam and level control module, with two control probes and two peristaltic pumps for the addition of antifoaming and water, mechanical shaker with speed between 100 and 1200 rpm, shaking shaft with two 74 mm Rushton helices (six blades), rotameter to control aeration range between 0 and 15 l/min and 1 by 1 scale. Yeasting standards were temperature of 30° C., pH 5.0 controlled by the addition of 5% phosphoric acid and/or 3 normal sodium hydroxide, 30% $dO_2$, speed between 100 and 1200 rpm, automatic control according to oxygen saturation and 1 vvm variation (5 to 10 l/min according to the volume of the medium).

TABLE 4

MEDIA USED TO PRODUCE OIL-PRODUCING BIOMASS IN THE BIOREACTOR

| X (Pre-inoculate) | Y (Medium of Adaptation) | Z (Medium of Production) |
|---|---|---|
| Glucose, 10 g/l | Sugar cane molasses, 10 g/l | Sugar cane molasses, 40 g/l |
| Peptone, 5 g/l | Concentrated and detoxified sugar cane bagasse hydrolysate, 5 g/l | Concentrated and detoxified sugar cane bagasse hydrolysate, 30 g/l |
| Yeast extract, 3 g/l | Glycerol, 5 g/l | Glycerol, 30 g/l |
| Malt extract, 3 g/l | Yeast extract, 5 g/l | Yeast extract, 5.0 g/l |
| pH 5.0 | pH 5.0 | Urea, 2.5 g/l |
| | | Antifoaming, 0.5 ml/l |
| | | pH 5.0 |

Figure 4:
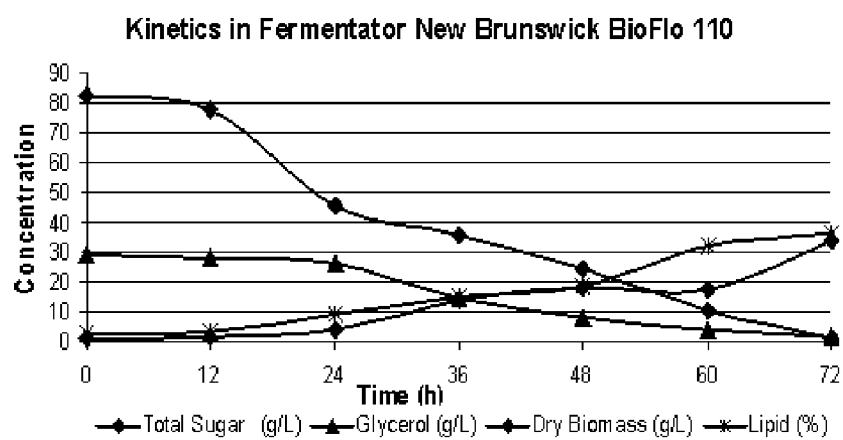
FIG. 4 shows the profile of kinetic evolution of the main production standards of oil-producing microbial biomass.

Table 5 below and FIG. 4 show the evolution of the main kinetic standards, as well as global yieldings of said yeasting in a bioreactor. Results obtained show that about 29.95% of carbon sources (Table 4, Medium Z) were used by the yeast for production of biomass and about 10.81% for production of lipids. Total biomass as produced in a bioreactor was about 22.21% higher than produced in Erlenmeyer flasks in similar culture medium (Table 3, Culture Condition 13), while the accumulation of lipids in the biomass was about 7.5% higher.

TABLE 5

EVOLUTION OF MAIN KINETIC STANDARDS IN THE BIOREACTOR

| T (h) | pH | Total Sugar (g/l) | Glycerol g/l | Dry Biomass (g/l) | Lipids % | Global x/s Yeast (%) | Global p/s Yeast (%) |
|---|---|---|---|---|---|---|---|
| 0 | 5.0 | 82.40 | 29.04 | 1.32 | 2.68 | | |
| 12 | 5.0 | 77.90 | 28.22 | 1.94 | 3.47 | | |

TABLE 5-continued

EVOLUTION OF MAIN KINETIC STANDARDS IN THE BIOREACTOR

| T (h) | pH | Total Sugar (g/l) | Glycerol g/l | Dry Biomass (g/l) | Lipids % | Global x/s Yeast (%) | Global p/s Yeast (%) |
|---|---|---|---|---|---|---|---|
| 24 | 5.0 | 45.33 | 26.48 | 3.92 | 9.25 | | |
| 36 | 5.0 | 35.63 | 14.63 | 14.25 | 15.22 | | |
| 48 | 5.0 | 24.72 | 8.33 | 17.93 | 18.5 | | |
| 60 | 5.0 | 10.45 | 4.15 | 17.76 | 32.22 | | |
| 72 | 5.0 | 1.39 | 2.02 | 33.67 | 36.13 | | |
| | | | | | | 29.95 | 10.81 |

In the process of the present invention, there are concrete possibilities to use, as substrates for the production of oil-producing biomass from yeast, residues from sugar cane industrialization, such as sugar cane molasses and concentrated and detoxified sugar cane bagasse hydrolysate, as well as glycerol, a residue from the transesterification of triacylglycerols during the production of biodiesel. Said residues may be used isolated or in combination under various proportions, together with different sources of nitrogen of organic or inorganic origin or their combinations, with the purpose to always reach high concentrations of biomass containing high contents of lipids, as shown by the experiments of the present invention as disclosed above. Higher and/or lower values than presented in said examples of experiments may be obtained as a function of physical/chemical and nutritional conditions, equipment, microorganisms, optimizations and improvements which may be made to the process of the present invention.

The production of oil-producing microbial biomass of the present invention may be effected by using other genus and species of filamentous fungi and yeasts, be them genetically modified or not. Preferably, groups of filamentous fungi and yeasts are composed by *Candida curvata, Candida guilhermondi, Candida tropicalis, Candida* sp., *Candida oleophila, Candida lipolitica, Cryptococcus terricolus, Hansenula saturnus, Hansenula ciferrii, Lipomyces starkeyi, Rhodosporidium toruloides (Rhodotorula gracilis), Aspergillus fischeri, Aspergillus fumigatus, Aspergillus nidulans, Aspergillus ochrceus, Aspergillus terreus, Aspergillus ustus, Cladosporium falvum, Cladosporium herbarum, Mucor miehei, Penicillium gladioli, Penicillium javanicum, Penicillium lilacinum, Penicillium spinulosum, Penicillium ultimum, Cryptococcus albidus, Rhodotorula glutinis, Trichosporon pullulans, Mortierrella hygrophila, Mortierrella zychae, Mortierrella elongata, Mortierrella parvispora, Mortierrella schmuckeri, Mortierrella alpina, Lypomyces lipofer, Lipomyces tetrasporus, Williopsis saturnus, Candida diddensiae, Yarrowia lipolitica,* and *Trichosporon cutaneum,* among others, are all able to accumulate lipids in their biomass during the growth and post-growth stages. These microorganisms are used isolated or in associations of two or more.

Said filamentous fungi and yeasts may be cultivated in different models of bioreactor, including shaked tank, bubble column, airlift, packed bed, fluid bed or dripping bed, operating in batches, fed batches or continuously. Culture media as shown by Tables 3 and 4 may or not be supplemented with a mineral or organic source of nitrogen, such as ammonia, ammonium sulphate, ammonium phosphate, soy grits, meat extract, soy protein hydrolysates, besides $KH_2PO_4$, $K_2SO_4$, $MgSO_4$, $ZnSO_4$, $CuSO_4$, $FeSO_4$, other minerals and oligo-elements. During the formation of biomass and the accumulation of lipids by microbial cells, carbon/nitrogen ratio between 0.5 and 500, pH between 2.5 and 8.5 and temperature within the range between 10 and 50° C. may be used in the bioreactors. Culture medium based on sugar cane derivatives, their hydrolysates of bagasse and glycerol may or not be pasteurized or sterilized by using heat as a form to eliminate the microbial load as naturally present but undesirable in raw materials. In case of practice of pasteurization or sterilization, the temperature may vary between 62 and 142° C. under time of thermal exposure between a few seconds and a few hours, as a function of the used technique. Media may also be treated with antibiotics and antifungics to reduce the undesirable microbial load as present in substrates. In case of use of antibiotics, they should have wide spectrum, i.e. be active against Gram (+) or Gram (−) bacteriae. After pasteurization and/or sterilization, culture media based on sugar cane derivatives will be cooled at temperatures between 15 and 50° C. Culture media intended for the production of microbial biomass and consequent lipid production will be inoculated with strains of oil-producing fungi and/or yeasts and cultivated in bioreactors with lower volume, with medium of equal and/or different composition to the above disclosed. It is important that such inoculates have high concentrations of viable cells, higher than about $10^3$ UFC/$cm^3$, and may even reach values of about $10^{12}$ UFC/$cm^3$ or more. The volume of inoculate as used in production tanks may vary between 1 and 99% of the volume of work of the production bioreactor, always depending on the used system, i.e. batches, fed batches or continuous system. The culture medium inside the bioreactor will have controlled temperature of 15 to 50° C. through heating/cooling serpentines or blankets, through which cold water or steam may circulate. pH inside the bioreactor will be kept within the range of pH 2.5 to 8.5 as a function of the microbial strain used and will be made by pumping a solution containing concentrated alkali or acid. Culture medium inside the bioreactor may be mechanicall shaken or not. In case of using shaking, it should be made by means of a blade system at a speed which may vary between 5 and 500 rpm. Culture medium for the production of oil-producing microbial biomass is aerated with a volume of air within the range of 0.1 to 5 v/v/m (volume of air per volume of medium per minute). Just air may be used, or a mixture of air/oxygen, or just oxygen. Air injection inside bioreactors will be made by compressors and all the air will be filtered through filters able to retain particles of up to 0.2 μm. The time for cultivation for the production of biomass and lipid accumulation will be variable and within the range between 24 hours and about 150 hours, as a function of the genus and species of the microorganism, as well as the cultivation system and the model of bioreactor as used, and may even be of weeks or months, in case of cultures operating in continuous system.

The microbial biomass as produced by Unit 2 may reach concentrations between 15 and 130 g/l, depending on the used technique of cultivation, and the accumulation of lipids may reach concentrations of up to 65% or more over their weight.

$3^{rd}$ Step—Cultivation and Recovery of Algal Biomass

Figure 5:
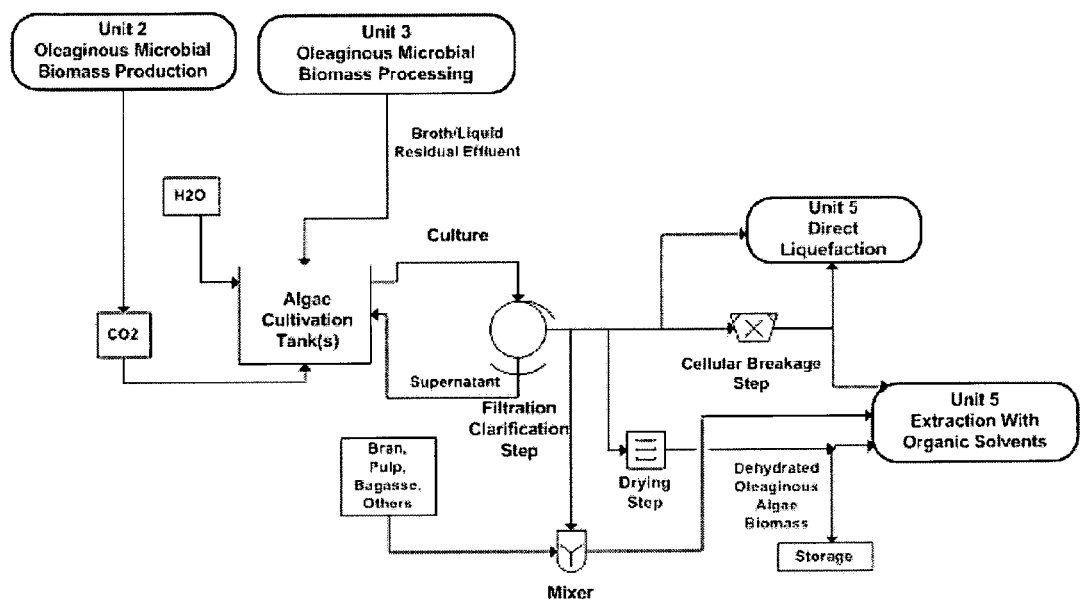
FIG. 5 shows a flow chart of the units of cultivation and recovery of algal biomass.

In Unit 4—Cultivation and Recovery of Algal Biomass, integrated to the process of the present invention, the broth is prepared, a liquid effluent resulting from the production of oil-producing biomass from the yeast *Rhodosporidium toruloides* OF A25 for use as a substrate in microalga cultivation. FIG. 5 shows a flow chart of the integration of Unit 4 to the process of the present invention as disclosed above.

In development studies of the process of the present invention, we have concluded that the broth, a liquid effluent originating from the separation of oil-producing microbial biomass, be it produced by filamentous fungi or yeasts, is an excellent substrate for the cultivation of microalgae, be them oil producers or not. In the example of experiment of the present invention, the broth from the production of oil-producing biomass from Rhodosporidium toruloides OF A25 as produced in a bioreactor was used for said purpose. That broth had its physical/chemical composition analysed and was used as a substrate in the cultivation of the microalga Botryococcus braunii OF C27 in the examples of experiments as presented below. Broth has, as shown by Table 6 below, besides water, considerable concentrations of mineral salts and organic components, such as residual sugar not consumed by yeasts, biomass and fragments from yeast cells, soluble proteins, etc. Therefore, for being rich in organic matter and minerals, said broth equally has significant pollutant load, with BOD (Biochemical Oxygen Demand) and COD (Chemical Oxygen Demand) of more than about 13,000 mg/l, which is considered as very high, environmentally speaking.

TABLE 6

COMPOSITION OF FERMENTED BROTH OF
RHODOSPORIDIUM TORULOIDES OF A25*

| Components | Concentration (mg/l) |
| --- | --- |
| BOD | 13.900, 08 |
| COD | 23.414, 04 |
| Chlorides | 0.00 |
| Sulphates | <700.00 |
| Total Nitrogen | 30.00 |
| Organic Matter | 2.8% |
| Residual sugar | <1000 |
| Manganese | <0.20 |
| Potassium | 307.64 |
| Sodium | 153.45 |
| Zinc | <0.20 |
| Aluminum | <10.00 |
| Calcium | 134.38 |
| Cobalt | <0.50 |
| Copper | <0.50 |
| Iron | 1.17 |
| Phosphorous | 36.46 |
| Magnesium | 145.50 |
| pH | 5.0 |
| Density | 1035 |

*Analysis made by CEPRA (Center for Food Research and Processing - Federal University of Parana)

As generally known in the art, industries producing biological yeast (biomass) for bread production or as additives for animal food based on yeasts of the genus Saccharomyces, besides others, also discard that same type of liquid residue after the biomass is separated. The only and traditional destinations of said residue are industrial effluent treatment stations, where aerobic and anaerobic digestion systems are employed as a form to reduce the pollutant load in terms of DBO and DQO.

As an alternative to the discharge of effluent broth caused by the separation of microbial biomass, the process of the present invention incorporates said broth as a culture medium for algae, as a form to reduce the pollutant load, as well as to produce lipids, besides providing for the release of oxygen by said algae to the environment.

Nutritional elements present in said broth, particularly mineral salts, make them become an excellent substrate for the cultivation of various groups of oil-producing algae or not, which yieldings obtained in terms of biomass are compatible to classical media as disclosed by international literature. We have also surprisingly discovered that said liquid effluents originating from the filtration of biomass from yeasts may be used for the cultivation of algae for the production not only of lipids, but also proteins and other commercially interesting products.

Adaptation of Microalgae to the Broth

Previous adaptation studies of the microalga Botryococcus braunii OF C27 were made under growing mixtures of 5, 10, 20, 30 and up to 100% broth to the ESP culture medium, as shown by Table 7 below. Said adaptation was made in 250 ml Erlenmeyer flasks containing 50 ml of medium. Flasks were transported to a shaking incubator, trademark TECNAL, model TE-421, with controlled photo period, temperature and shaking. Cultures were incubated for a 15-day period, during which the following preferential standards were kept as constant: temperature 25° C. (±2° C.), 110 rpm shaking, 1500 Lux light irradiation intensity for 12 hour periods alternated with 12 hours in darkness. The light intensity inside the incubator was evaluated daily, in this case using a digital light meter Minip MLM 101. To follow the growth of algae, samples were taken every two days for analysis by dry weight. The algal biomass was vacuum filtered through 50 μm filter paper and subsequently washed with distilled water and dried for 24 hours in a oven at 100° C. Results show the average of two determinations. This process to previously adapt microalgae to the broth allowed to obtain more expressive results in terms of daily final yielding of biomass, as well as higher reduction rates of BOD and COD, in comparison with a process in which algae did not suffer this previous adaptation.

TABLE 7

COMPOSITION OF THE ESP MEDIUM USED IN
THE CULTIVATION AND ADAPTATION TO THE BROTH
OF BOTRYOCOCCUS BRAUNII OF C27

| Components | Stock solution (g/100 ml) | Nutritious solution (ml) |
| --- | --- | --- |
| $KNO_3$ | 1 | 20 |
| $K_2HPO_4$ | 0.1 | 20 |
| $MgSO_4 \cdot 7H_2O$ | 0.1 | 20 |
| Soil extract* | — | 30 |
| Micronutrient solution** | — | 5 |
| Distilled water | — | 905 |
| Proteose-Peptone | — | 1 |

Preparation of Inoculation

The inoculation for the cultivation of Botryococcus braunii OF C27 in broth may be made in different models of flasks made of glass or other light transparent material. The experiment of the present invention was made in 500 ml Erlenmeyer flasks containing 90 ml broth or a mixture of broth+water. Flasks containing said medium may or not be sterilized. In case of the experiment of the present invention, no sterilization was made, and said flask was inoculated with 10 ml of an active culture of Botryococcus braunii OF C27 adapted in a medium containing ESP+broth, so that the initial algal biomass concentration reaches values of at least 0.2 g/l. Similar processes may be conducted by using higher and/or lower algal biomass concentrations, by using or not previous adaptation of the alga to the broth, but the object is to always have vigourous inoculate with good quality to meet the requirements of the following step of the algal culture in broth. Flasks are transported to a shaking type incubator and cultivated at the same conditions as disclosed above. Algal biomass as obtained was used to inoculate tubular photobioreactors in the following steps.

Cultivation of *Botryococcus braunii* of C27 Under Growing Broth Concentrations

Microalga *Botryococcus braunii* OF C27 is cultivated in pure broth or diluted in water as the only substrate from the culture medium. Photobioreactors were filled in with 1.8 l non-sterilized broth, inoculated with an active culture of *Botryococcus braunii* OF C27 so that the concentration of algal biomass at the start of the culture is of about 0.2 g/l. Shaking and aeration of photobioreactors is made by means of a flow of 1 v/v/m atmospheric air (volume of air per volume of medium), by using glass canes with porous stones at their ends as a form to improve the diffusion of gases in the liquid medium. Experiments are conducted in a climate controlled room, with controlled temperature of about 30° C. (±2° C.) by using air conditioning. Two ovens are installed in that room with photo periods for time control digital cyclomatic trademark Full Gauge, model PROGS I with direct supply of 220 VCA containing twelve 20 Watt daylight fluorescent lamps. The illumination of photobioreactors is of 1500 Lux as supplied by daylight type fluorescent lamps for a twelve-hour period, alternated with twelve hours of darkness. Time for culture is about fifteen days. Volume of cultures was kept constant by daily reposition of distilled water to compensate losses for evaporation.

TABLE 8

CULTIVATION OF THE MICROALGA *BOTRYOCOCCUS BRAUNII* OF 8 UNDER GROWING BROTH CONCENTRATIONS

| Broth (%) | $H_2O$ Distilled (%) | EPS Medium Nutritious solution | Initial algal biomass (g/l) | Final algal biomass (g/l) | Lipids % | Lipids g/l |
|---|---|---|---|---|---|---|
| 25 | 75 | — | 0.203 | 2.985 ± 0.03 | 19.07 | 0.57 g/l |
| 50 | 50 | — | 0.212 | 3.162 ± 0.15 | 15.05 | 0.47 g/l |
| 75 | 25 | — | 0.195 | 4.18 ± 0.13 | 13.19 | 0.55 g/l |
| 100 | 0 | — | 0.207 | 6.17 ± 0.44 | 11.04 | 0.68 g/l |
| — | — | 100 | 0.212 | 1.322 ± 0.11 | 29.20 | 0.38 g/l |

The algal biomass as formed was vacuum filtered through 50 μm filter paper and subsequently washed with distilled water and dried for 24 hours in an oven at 100° C. Results express the average of two determinations for each experiment. We can notice from Table 8 above that the best result in tems of algal biomass as produced after fifteen days of culture was obtained with 100% pure broth (6.17 g/l). We can notice, however, that under that condition lipid percentage as present in the algal biomass was about 11.04%, lower than 19.07% as obtained in the experiment with diluted broth in 75% water. If the calculations are made in terms of lipid yielding per liter of culture medium as used, however, this situation becomes inverse. We therefore notice that the production of lipids was of 0.68 g/l when *Botryococcus braunii* OF C27 was grown in medium containing 100% broth, against 0.57 g/l when the medium was composed by 25% broth+75% $H_2O$. The quantity of biomass and lipids as produced by the microalga *Botryococcus braunii* OF C27 when cultivated in pure or diluted broth was higher than the medium (EPS—nutritious solution), indicated in the literature as ideal for the cultivation of that species of microalga (Table 8). From the results obtained, it is possible to conclude that the residual broth originating from the culture of pure or diluted oil-producing yeasts (Unit 2) constitutes an excellent substrate for the cultivation of microalga *Botryococcus braunii* OF C27, aiming to the complementary production of biomass and lipids, according to the integrated process object of the present invention.

Effect of $CO_2$ in the Culture of *Botryococcus braunii* of C27 in Broth

In the above description, it is possible to verify that the yielding of oil in g/l is more significant when the microalga *Botryococcus braunii* OF C27 is cultivated in medium containing 100% broth. We therefore attempted to evaluate the effect of $CO_2$ in the formation of biomass and lipid synthesis. Different $CO_2$ concentrations have been mixed with the feeding air from tubular photobioreactors during the cultivation of *Botryococcus braunii* OF C27 in pure broth. $CO_2$ originating from a gas cylinder is conducted to a gas mixer, which is simultaneously fed with air, so that gaes at the exit of the mixer present concentrations of 5%, 10% and 15% $CO_2$. Experiments are conducted in 15 (fifteen) day batches in 52 cm long glass tubular photobioreactors with 8 cm diameter and total volume of two liters (1.8 liters of working volume). All cultures were kept in constant shaking provided by flow of 1.0 v/v/m filtered atmospheric air. Cultivations were started with algal cell concentration of about 0.20 g/l and were kept during the experiment with no pH correction or adjustment. Culture volumes were kept constant by means of daily reposition of water as lost by evaporation. Inoculation and incubation conditions of photobioreactors were the same as used above. All the experiments were conducted in duplicate and results express the average of said determinations.

TABLE 9

EFFECT OF THE PRESENCE OF $CO_2$ IN THE GROWTH OF *BOTRYOCOCCUS BRAUNII* OF C27 IN BROTH

| Condition of the culture | Initial algal biomass (g/l) | Final algal biomass (g/l) | % Lipids |
|---|---|---|---|
| Air | 0.207 | 6.17 ± 0.44 | 11.04 |
| Air + 5% $CO_2$ | 0.199 | 6.54 ± 0.34 | 11.56 |
| Air + 10% $CO_2$ | 0.197 | 6.74 ± 0.27 | 11.87 |
| Air + 15 $CO_2$ | 0.205 | 6.68 ± 0.53 | 12.79 |

Table 9 above show obtained results. We conclude that the addition of $CO_2$ has a positive effect on the production of biomass and accumulation of lipids during the cultivation of the microalga *Botryococcus braunii* OF C27 in a medium based on residual broth from the production of biomass from oil-producing yeast. By comparing cultures in which $CO_2$ was mixed with air to the one receiving just atmospheric air, we can conclude that the higher concentration in terms of algal biomass and accumulated lipids (6.68 g/l biomass with 12.79% lipids) after fifteen days of culture in tubular photobioreactor was obtained with the mixture (Air+15% $CO_2$), while just with air it was 6.17 g/l. Higher and/or lower values to those ones may surely be obtained when cultures of the microalga *Botryococcus braunii* OF C27 or with other genus and species of algae when cultivated in pure or diluted broth, as well as at $CO_2$ levels not tested in this assay.

Recycling of Supernatant

The culture of the microalga *Botryococcus braunii* OF C27 is made by recycling the supernatant after separation, e.g. by filtering. The supernatant was recycled in the same photobioreactors as disclosed above, fed in all experiments with just one gaseous mixture (Air+15% $CO_2$), as this condition supplied the best results in terms of biomass production and lipid accumulation, although it is possible to use other concentrations of $CO_2$. Therefore, in the process of the present invention, recycling of the liquid fraction (supernatant) from the first production for use as a culture medium for a second, third or more batches, until the residual supernatant is fully exhausted of its original nutrients, is previewed.

After culture and filtration, the supernatant may have its pH changed, and its correction to an optimum range is required. The great advantage of said recirculation refers to the fact that, besides the biological treatment granted to said highly pollutant residue originating from Unit 2, we can implement the production of lipids intended to produce biodiesel and/or fuel oil. Table 9 below shows that, after a few cycles, macro and microelements are gradually consumed, COD and BOD levels are significantly reduced and reach levels very near zero after the third cycle. We can therefore clearly notice the economic and environmental importance of the recovery of $CO_2$ as generated during the production of biomass from the yeast *Rhodosporidium toruloides* OF A25 and its reuse for the production of biomass from the microalga *Botryococcus braunii* OF C27, thus reusing all residues as generated from Unit 2 in an integrated circuit.

TABLE 10

PRODUCTION OF ALGAL BIOMASS ALONG THE RECOVERY CYCLES OF BROTH FOR THE PRODUCTION OF BIOMASS FROM OIL-PRODUCING YEASTS

| Time of cultivation (days) | Air + 15% $CO_2$ g/l | % Lipids |
|---|---|---|
| 0 | 0.211 | — |
| 15 | 6.68 ± 0.53 | 12.79 |
| 30 | 4.54 ± 0.34 | 15.74 |
| 45 | 1.94 ± 0.27 | 17.65 |

Table 10 shows that recycling the supernatant has positive consequences to the rate of accumulation of lipids from *Botryococcus braunii* OF C27, but not to the production of biomass.

TABLE 11

REDUCTION OF COD AND BOD LEVELS FROM THE BROTH ORIGINATING FROM UNIT 2 ALONG THE CYCLES

| | DQO (mg/l $O_2$) | DBO (mg/l $O_2$) |
|---|---|---|
| Beginning | 23.414 ± 724 | 13.900 ± 589 |
| $1^{st}$ Cycle | 4682 ± 234 | 1210 ± 65.7 |
| $2^{nd}$ Cycle | 265 ± 67 | 97 ± 3.12 |
| $3^{rd}$ Cycle | 24 ± 1.57 | <5.0 |

BOD and COD analysis, which results are listed on Table 11 above, have been taken according to Standard Methods for the Examination of Water and Wastewater, 20 ed., 1998, Hach Company and WTW. The full quantity of lipids as present in algal biomass was determined by using the methods proposed by BLIGH & DYER (1959).

Furthermore, according to the present invention, the residual broth may be diluted in water, adding or not other chemicals with the purpose to adjust its pH or even complement given macro and micronutrients. Also, if required, broth may be decanted, filtered or clarified by using activated carbon or flocculant agents, depending on the concentration of solids in suspension. We also notice that pasteurization or sterilization of juice does not provide for significant difference in biomass production and lipid accumulation in the various groups of researched algae, and therefore a unit operation is not required, although it may be used when necessary.

According to the present invention, this same methodology may be used for other algae and/or cyanobacteriae which may be cultivated isolated and/or in cocultures (combined strains) and are preferably from genus and species formed by the group *Euglena* sp. (*gracilis*), *Anabaena* sp. (*variabilis, cylindrica, hassali, planctonica*), *Dunaliella* sp. (*salina, bardawil, tertioleta*), *Achananthes orientalis, Amphora* (*delicatissima, cafeiformis*), *Ankistrodesmus falcatus, Chaetoceros* sp. (*muelleri, gracilis, muelleri subsalsum*), *Clorococcum* sp., *Chlorrella* sp. (*ellipsoidea, salina*), *Chromonas* sp. *Chrysosphaera* sp., *Cricophaera* sp., *Cryptomonas* sp., *Cyclotella* sp. (*meneghiniana, cryptica*), *Navicula* sp. *Amphiprora hyalina, Eustigmatophyte flagellate, Pleurochysis* sp., *Franceia* sp., *Gleocapsa* sp., *Gloeothamnion* sp., *Hymenomonas* sp., *Isochrysis* aff. *Galbana, Monoraphidium* sp., *Nannochloropsis* sp. (*salina*), *Navicula* (*saprophil, pseudotenelloides, biskanterae, acceptata, saprophila, pseudotenelloides*), *Nephrochloris* sp., *Nitzschia* sp. (*pusilla monoensis, elliptica, alexandrina, quadrangula, pusila monoensis, inconspicua, microcephala, frustulum, hantzchianna, intermedia, frustulum, communis*), *Ochromonas* sp., *Oocystis* sp. (*pusilla*), *Oscillatoria* sp. (*subborevis, limnetica*), *Phaeodactylum tricornutum, Platymonas* sp., *Pleurochrysis* sp. (*dentate*), *Prymnesiophyte* sp., *Pseudoanabaena* sp., *Pyraminonas* sp., *Stichococcus* sp., *Synechococcus* sp., *Tetraselmis suecica, Thalassiosira weissflogii, Nitzschia* sp., as well as their mutants and/or genetically changed strains able to accumulate lipids in their biomass.

Said algae and cyanobacteriae may also be cultivated in industrial scale. Different shapes and sizes of tanks may be used, which may be open or closed, aerated or not, shaken or not, continual, semicontinual or discontinual, horizontal, vertical, raceway type, in plates or tubes, oval, circular, rectangular or square.

The cultivation of algae or cyanobacteriae in open reactors is made in natural or artificial tanks under volumes which may vary between some dozen liters up to several million liters. Said reactors occupy large areas and may reach, in average, 10,000 m² or more, in case of one single horizontal or vertical tank. The most common shaking system uses blades, which are mechanically shaken and distributed in regular spaces throughout the surface of the medium, or then located at the ends or in the center of the reactor. Jointly with blade shaking, compressed air may be injected. Such air may be filtered or not. Reactors may be closed by using a removable cover, but for obvious reasons, such cover shall be constructed with transparent or translucid material to natural or artificial light. Appropriate materials are plastic, acrylic and glass.

In case of industrial production, carbon dioxide ($CO_2$) as produced by Unit 2—Production of oil-producing microbian biomass, is recovered at the top of bioreactors by means of a collector coupled to it and transported through pipings until alga and/or cyanobacteria production tanks. $CO_2$ is distributed through appropriate bubblers or diffusers installed in the culture medium, so that $CO_2$ concentration as dissolved in the medium is about 0.1 to 30%. $CO_2$ may be pressed and/or purified and stocked in pressurized reservoirs before being injected into alga and/or cyanobacteria cultivation tanks. In case of purification, gases originating from bioreactors to produce oil-producing microbial biomass (Unit 2) pass through two washing towers filled in with ceramic spirals until reaching the gas meter. On said towers, where the washing liquid is dearated water, all hydrosoluble impurities are almost fully removed. The washing liquid returns by pumping to microbial biomass production bioreactors (Unit 2), and may also be sent to algal biomass production tanks. From the gas meter, the gas is conducted to a depurating device containing $K_2Cr_2O_7$ in solution, which oxidizes volatile metabolites such as aldehydes, alcohols and others, present in the gas, which is then cooled. In a second depurating device, containing $H_2SO_4$, oxidation is complete and the gas is dehydrated. $CO_2$ exiting from said depurating device drags a bit of acid which is eliminated in a tower filled with coque, wherein a $Na_2CO_3$ solution is circulated. When the acid is neutralized, $CO_2$ is released. The gas passes through a washer containing a small portion of glycerin having the purpose to absorb the oxidized products and supply an odorless gas which may be stocked under compression in tanks to be used in the cultivation of algae and/or cyanobacteriae.

The separation or harvest of algal biomass as produced may be made continuously, semicontinuously or discontinuously, manually or mechanically, flocculated or not, by using centrifuges, filters, press filters, screens, decanters or vortexes. Centrifugation and/or filtering is preferred, according to the process of the present invention. Algal biomass may be extruded or not, dried naturally or in fixed or mobile bed driers, or by atomization (spray drier) or rotating drum to later extract lipids. Algal oil-producing biomass as recovered may also alternatively be submitted to a cell disrupting step and subsequently sent to a mixer.

4$^{th}$ Step—Processing of Oil-Producing Microbial and/or Algal Biomass

Both the oil-producing biomass and the algal biomass produced according to the process of the present invention are separated from the culture broth of the same form, i.e. by centrifugation. In experiments, a centrifuge trademark Car Padberg Zentrifugenbau, model 241, 20,000 rpm, capacity 250 l/h, was used. After separation of the broth, said biomasses have been washed twice with drinkable water. Said biomasses may also be separated by other unitary operations, such as decantation or filtering, although spinning may be the preferred process in the present invention. In the present case, biomass was processed by two different methods, with and without drying.

Drying

Drying of algal and oil-producing yeast biomasses was made in a vacuum oven trademark BTM Medical, Model Vacucell, with capacity for 111 liters. It was dried at a temperature of 60° C., pressure of 500 mmHg and 24-hour time. After drying, the humidity content of said biomasses vary between 8.5 and 10%.

Treatment of Wet Biomass

Figure 6:
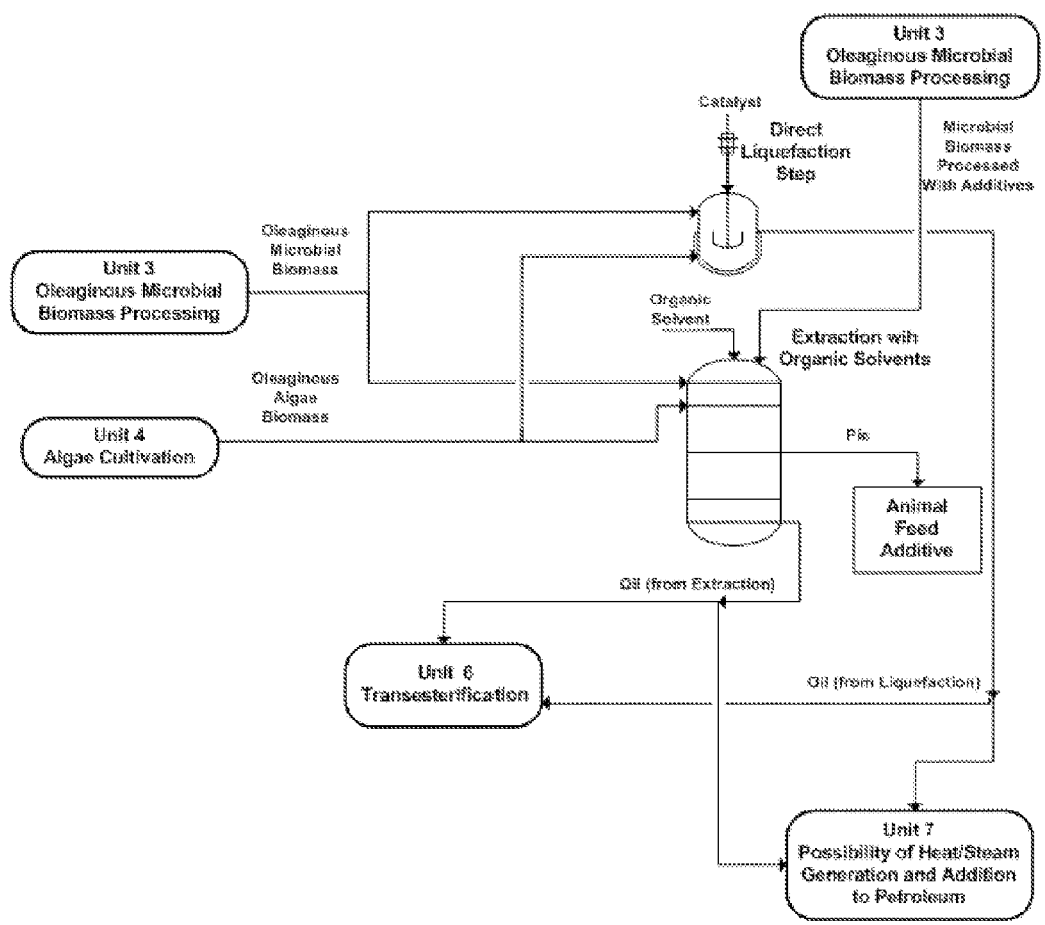
FIG. 6 shows a flow chart of the step of lipid extraction and direct liquefaction of oil-producing microbial biomass and algal biomass.

Biomasses of oil-producing and algal yeast recovered after spinning are sent to Unit 5—Oil Extraction (lipids) and Direct Liquefaction, as shown by FIG. 6. Alternatively, the wet or dry biomass may pass through a cell disruption process to facilitate the subsequent extraction of lipids in the extractor based on organic solvents. Said cell disruption may be effected by using mechanical or non-mechanical methods. Mechanical methods consist in the use of pressure, grinding or ultrasound. Non-mechanical methods are fundamentally based on the use of enzymes causing cell lysis, such as lysozyme or others, or in chemical methods by using detergents or in physical methods, by means of osmotic shock or freezing. Still wet biomasses (in paste) of algal and microbial nature submitted or not to cell disruption may also be optionally sent to a mixer where natural dehydrated supports are equally fed, such as soy grits, concentrated soy protein, citrus pulp and manioc bagasse, among others. The addition of said natural supports to the oil-producing biomass of filamentous fungi and/or yeast and/or algae has the object to suppress its drying step before being conducted to the extractor, also generating a product intended for animal consumption after lipids are extracted.

5$^{th}$ Step—Oil (Lipid) Extraction and Thermopressurized Direct Liquefaction Biomasses from oil-producing yeasts *Rhodosporidium toruloides* OF A25 and microalga *Botryococcus braunii* OF C27, produced and processed according to the present invention, have their oils (lipids) extracted by two different processes in a Soxhlet-type extractor and by direct thermopressurized liquefaction.

Semi-Pilot Soxhlet Type Extractor

A semi-pilot extractor based on Soxhlet methodology, with extraction chamber/vase containing a three-liter volume is fed with 300 grams of biomass of milled oil-producing yeast and algal biomass with 0.1-1 mm particles. Oil extraction (lipids) is made in that chamber by recirculating 2.5 liters of n-hexane percolating through the biomass as contained inside a filter paper enclosure. As a source of heating of the chamber, flowing steam is used at 4 atm. The extraction temperature as used in said extractor is 95° C., for optimized extraction time of four hours. Other solvents and/or extraction conditions may be tested in said equipment.

Analysis of Oils (Lipids)

Oils as produced by the yeast *Rhodosporidium toruloides* OF A25 and the microalga *Botryococcus braunii* OF C27 have been analysed as per the methods below:
1. methylation of fatty acids as present in the samples of algal and yeast biomasses by using the method Metcalfe, Smith & Pelka (1966);
2. separation and detection of fatty acids as present in the samples by using a Varian trademark chromatograph, model 3300, provided with flame ionization detector, "split/splitless" type injector, with column Carbomax 20M. Standards for operation: detector temperature—280° C.; injector temperature—250° C.; column temperature—110° C. (two minutes), scheduling at 5° C./min up to 180° C. (7 min), scheduling at 10° C./min up to 210° C.;
3. Dragging gas, $H_2$ with flow at the 1 ml/min column;
4. Make up gas, $N_2$ (30 ml/min); and
5. Split injection technique, ratio 1:100.

Retention time (tr) and percentage (%) of components were obtained by means of the INTRALAB 4290 integrator coupled to the chromatograph.

The identification of fatty acids as present in each sample was made by the following procedures:
i. retention time and corrected retention time (tr and trc) of methyl esters of fatty acids of samples and standards;
ii. coelution (spking) technique of standards with the sample; and
iii. equivalente chain length (ECL).

ECL values were calculated according to Miwa et al, 1960, Bano et al, 1988. Tables 12 and 13 show the average composition (three determinations) of the present fatty acids (in three different samples) of oils produced by the oil-producing yeast *Rhodosporidium toruloides* OF A25 and by the microalga *Bottyococcus braunii* OF C27.

TABLE 12

PROFILE OF FATTY ACIDS OF THE YEAST *RHODOSPORIDIUM TORULOIDES* OF A25

| Fatty acid | Carbon | g/100 g |
|---|---|---|
| Myristic | C 14:0 | 1.52 ± 0.07 |
| Palmitic | C 16:0 | 22.73 ± 1.77 |
| Palmitoleic | C 16:1 | 0.44 ± 0.04 |
| Stearic | C 18:0 | 15.25 ± 2.01 |
| Oleic | C 18:1 | 45.20 ± 1.89 |
| Linoleic | C 18:2 | 11.44 ± 0.94 |
| Linolenic | C 18:3 | 3.46 ± 0.41 |

TABLE 13

PROFILE OF FATTY ACIDS OF THE MICROALGA *BOTRYCOCCUS BRAUNII* OF C27

| Fatty acid | Carbon | g/100 g |
|---|---|---|
| Laurie | C 12:0 | 2.26 ± 0.16 |
| Myristic | C 14:0 | 2.92 ± 0.93 |
| Palmitic | C 16:0 | 39.26 ± 3.77 |
| Stearic | C 18:0 | 4.21 ± 0.644 |
| Oleic | C 18:1 | 23.09 ± 1.98 |
| Linoleic | C 18:2 | 13.44 ± 1.22 |
| Alpha linolenic | C 18:3 | 14.79 ± 0.95 |

Extraction by Direct Thermopressurized Liquefaction

This process is named extraction by direct thermopressurized liquefaction (ELDT), since the extractor/reactor operates under higher pressures than atmospheric. Said added pressure is not caused by the injection of an inert gas, but by the elevation above the ebullition and vaporizing point of the liquid inside the vase/reactor. The reactor is formed by a vase of carbon steel internally coated with stainless steel AISI 316. Said internal coating should be of stainless steel to avoid corrosion due to the various salts being added to the fermenting juice unavoidably present in considerable quantities in the wet biomass.

The extractor is constituted by a 40 cm long cylinder with 20 cm external diameter and 15 cm internal diameter, resulting in a total volume of 7.0 liters. There are three internal chicanes in 120° between them and 1 cm wide, enough to raise the spheres and make them fall. The reactor lays over horizontal axes moving them at a speed of 40 rpm, promoting efficient mixture between solvent, biomass and china spheres, providing better efficiency in cell disruption and facilitating oil extraction. 500 g of biomass from oil-producing yeasts and algae in paste form with 70% humidity are mixed with 2.1 liters of solvent and 50 china spheres. Under said operational conditions, the occupation rate of the working volume of the reactor is approximately 35%. The reactor is sealed and the extraction process starts, being effected at a temperature of about 120° C. for the use of n-hexane as the solvent or about 145° C. for the use of methanol. Pressure used for both treatments is 7 bar, as previously optimized. Temperatures and pressures higher and/or lower than these may be used. The extraction time is 1:30, as per previously optimized conditions.

After the end of the extraction, the solid fraction formed by cell debris is separated from the liquid fraction formed by oil+solvent+water, by means of vacuum filtration through Büchner filter with filter paper with 4 μm porosity. The solid phase is retained within the filter, dehydrated and may be used as a supplement for animal food. The mixture of the organic and oil phases is sent to a decanting funnel. After one hour, phases are well distinct. The upper layer is composed by a mixture of oil and solvent. Said mixture is distilled to recover the solvent which may be recycled in the process, to obtain a gross dark-colored viscous oil.

TABLE 14

PROPERTIES OF THE OIL AS OBTAINED BY DIRECT THERMOPRESSURIZED LIQUEFACTION (ELDT)

| Properties | OBL | OBM | *Fuel oil BPF (type A) |
|---|---|---|---|
| Apparent density (kg/m$^3$) | 957 | 945 | 970 |
| Kinematic viscosity (mm$^2$/s) | 194 | 189 | 620 (max) |
| Flash point Min. ° C. | 85 | 79 | 66° C. (min) |
| H$_2$O and sediments (% volume) | 1.22 | 1.69 | 2.0% (max) |
| Content of sulfur | 1.43 | 0.49 | 2.5% (max) |
| Heating power kcal/kg | **8598 | **8429 | 9600 |

*Normas ANP, Portaria 80, ASTM E 29 OBL = Óleo bruto de levedura, OBM = óleo bruto de microalga
**Poder calorífico inferior Table 14 above shows the properties of microbial and algal oils as obtained by the ELDT process, according to the present invention, in comparison with the BPF oil (type A), derived from petroleum. Experiments show that said oil as obtained from the yeast (OBL) and microalga (OBM) biomass are within Brazilian rules (ANP, Decree 80 and foreign ASTM) for this class of fuel intended to generate heat/steam. The ELDT process as disclosed above has large application potential in the field of biofuel production, since it eliminates the biomass drying operation, which is considered very expensive. Therefore, the present invention, by its integrated technologies, contemplates the possibility to choose the most economically advantageous technological route and/or tipe of biofuel which production is desired, biodiesel or fuel oil to generate steam/energy.

Furthermore, according to the process of the present invention, the algal and/or microbial oil-producing biomass with high humidity content may alternatively be liquefied in a reactor under pressure and temperature, in the presence of chemical catalysts, preferably in the presence of alkalis. During liquefaction, the reactor may be purged with an inert gas, such as nitrogen, since the purge avoids the water to evaporate and helps to remove residual air in the equipment. According to the provenience of the biomass (if microbial, algal or their mixtures), the direct thermopressurized liquefaction procedure may last between five and 120 minutes, the internal temperature of the reactor may vary between 120° C. and 400° C. and the internal pressure may vary between 1 MPa and 5 MPa. The liquefied material as obtained from this technique has high heating power, about 5,000 to 11,500 kcal/kg, depending on the content of lipids as present in the biomass, as well as the conditions used in the liquefaction process and nature of catalyst. The product as obtained may be directly used as a fuel or may be mixed to the fossil petroleum during the refining operation, with the purpose to increase diesel and/or gas fractions. It may also be sent to a new step of liquid-liquid extraction, aiming to extract hydrocarbons and subsequently produce biodiesel.

6th Step—Transesterification of Oils (Lipids) by Acid Catalysis

Lipids from yeast and microalgal oil-producing biomass as extracted and analysed as disclosed above were transesterified following a technique disclosed by Miao & Wu (2006).

Transesterification reactions were effected in Becker glass flasks with 1 liter capacity. Methanol:oil ratio of 56:1 and 100% $H_2SO_4$ were used as a catalyst. Flasks covered with aluminum foil were transported to a oven with controlled temperature at 30° C., being the transesterification reaction conducted under shaking for a period of four hours. After that period, the product of the reaction was transported to a separating funnel. The upper part constituted by biodiesel was separated and washed with petroleum ether and subsequently water at the temperature of 45° C. until it became neutral, showing that the residual acidity of the transesterification reaction was fully removed. Biodiesel was then obtained by separating petroleum ether by distillation. The lower part of the separation funnel is basically constituted by glycerin, which is recirculated to the reactor of Unit 2, thus effecting the cycle of full use of residues in the process of the present invention.

Evaluation of the Quality of Produced Biodiesel

Table 15 below shows a series of standards of biodiesel as produced from methyl esters obtained from oil-producing biomasses of the yeast *Rhodosporidium toruloides* OF A25 and microalga *Botryococcus braunii* OF C27. These results were compared with petroleum-based diesel purchased in the market in the city of Ribeirao Preto, State of Sao Paulo, Brazil. Results show that the quality of the biodiesel produced by means of the process of the present invention is similar to petroleum-based diesel, and may be used fully or in mixture with said fossil fuel in diesel type engines. Another possibility is its use as a substitute to biodiesel produced from agricultural products in wide demand for human and animal food, such as soy.

TABLE 15

COMPARISON OF PROPERTIES OF BIODIESEL PRODUCED FROM YEAST OIL AND MICROALGA WITH PETROLEUM-BASED DIESEL

| Characteristics | Used method/ technique | BL | BM | Diesel sold in the State of Sao Paulo - Brazil |
| --- | --- | --- | --- | --- |
| $H_2O$ + Sediments (% volume) | ASTM D 1796 | 0.03 | 0.01 | 0.03 |
| Ashes (% mass) | ASTM D 482 | 0.0 | 0.01 | 0.0 |
| Relative density at 20-4° C. (kg/m$^3$) | ASTM D 4052 | 875 | 869 | 852 |
| Flash point (min, ° C.) | ASTM D 56 | 103 | 96 | 59 |
| Viscosity at 40° C. | ASTM D 445 | 5.3 | 5.2 | 3.5 |
| Higher heating power (kcal/kg) | ASTM D 240 | 9860 | 9275 | 11300 |
| Cetane rate | ASTM 4737 ANP Decree 210/2001 | 46 | 45.5 | 44 |

ASTM: American Society for Testing and Materials.

Figure 7:
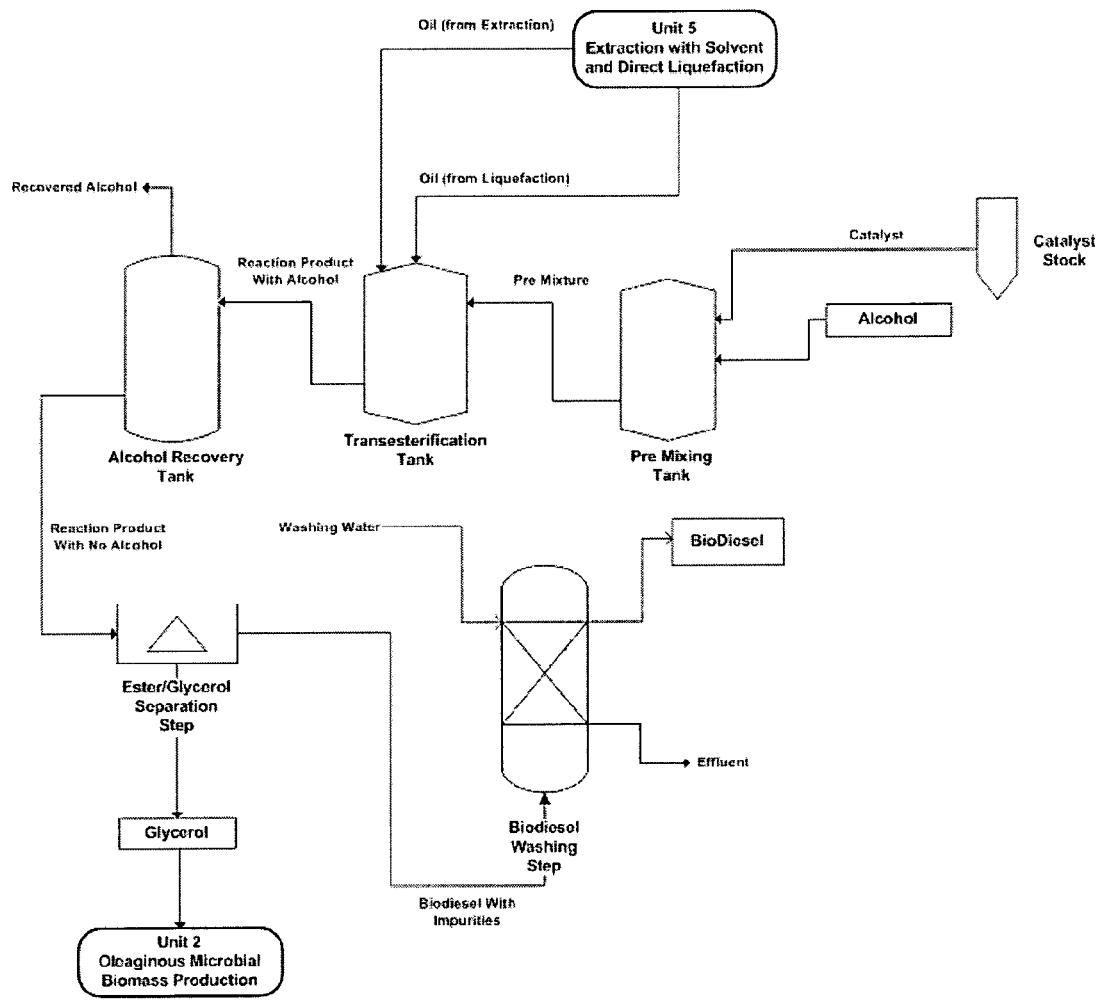
FIG. 7 shows a flow chart of the step of lipid transesterification.

According to another aspect of the present invention, transesterification of oils originating from one of the direct liquefaction or extraction subunits, or even their mixtures, may be transesterified by using ethanol, isopropanol, butanol or any other primary, anhydrous or hydrated alcohols, or their mixtures under any stoichiometric proportions of oil/alcohol. Temperature of reaction should be between 25° C. and 120° C. FIG. 7 shows a flow chart of the transesterification unit, an integral part of the present process.

In said Unit 6, transesterification may also be effected by using different chemical catalysts. If the catalysis is alkaline, sodium hydroxide, potassium hydroxide or others may be used and, if the catalysis is acid, phosphoric acid, hydrochloric acid, calcium carbonate or others may be used. In case of enzymatic catalysis, any enzymes classified as lipolytic/lipase may be used. According to the catalyst as used in the process, the corresponding neutralizer should be applied at the biodiesel washing step. Transesterification may also be effected by using co-solvents such as tetrahydrofuran or others, which will increase the solubility of the primary alcohol as used. In this case, neutralization is not required, since they are recovered jointly with the alcohol.

Besides these two options, there is a third one, the transesterification reaction under supercritical state, wherein reaction will occur at temperatures between 350° C. and 400° C. and pressures within the range of 60 to 100 atm.

Generally speaking, transesterification reaction may also occur in batches or in a continuous system. Catalyst, co-solvent, alcohol and the processed biomass may be added to the transesterification tank jointly or previously mixed in another order by using additional tanks for said mixtures. Reaction may occur with or without homogeneous or heterogeneous acid, basic or enzymatic catalysis, with or without the use of co-solvents, in supercritical state or not and with or without shaking.

After the step of transesterification, the alcohol used may be recovered by evaporation or flash distillation processes, aiming to reduce the solubility of glycerol in biodiesel. If transesterification with cosolvent is used, in this step it will be removed with alcohol.

After the transesterification step, phases are separated, thus resulting in a light phase comprising biodiesel (upper phase) and a heavy phase comprising glycerol (lower phase). Phase separation may occur naturally by decantation or by the action of a centrifugal gravitational field to accelerate that process, and a centrifuge may then be used. After phase separation, glycerol is taken from the system and recirculated as a source of carbon for the production of oil-producing microbial biomass, at the start of the integrated process of the present invention. Biodiesel thus obtained alternatively passes through a washing step, aiming to remove any impurities or other chemical compounds added to the process. Such washing is made by using different water/biodiesel proportions and by any appropriate method. The effluent in that washing step consists of a mixture of water and catalyst, in case it has been employed in the transesterification step.

Purified biodiesel may then be stored or, if a product with higher quality is desired, it may also be submitted to a step of evaporation of the remaining water.

Figure 8:
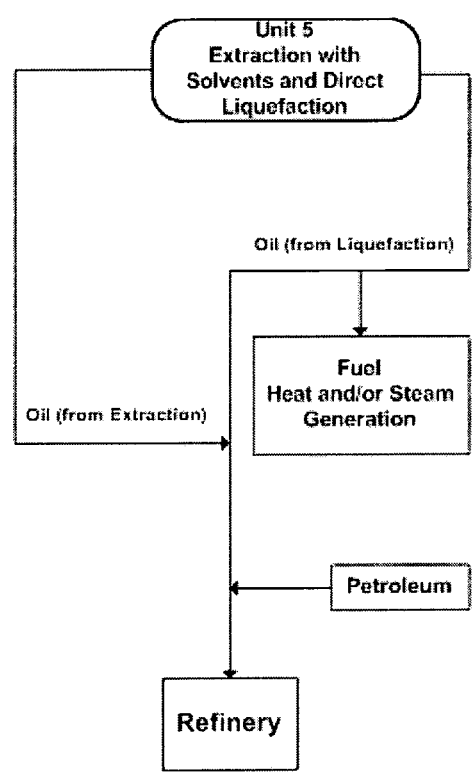
FIG. 8 shows a flow chart of an alternative use of lipids.

As an alternative to biodiesel production, lipids originating from Unit 5—Oil (lipid) Extraction and Direct Thermopressurized Liquefaction as shown by FIG. 6 and disclosed above may be directly used in the industry. Advantageously, lipids originating from the subunit of direct liquefaction may be used as fuel to generate heat and/or steam, while lipids originating from the subunit of extraction or its mixtures with those originating from the subunit of direct liquefaction may be used as adjuvants to gross petroleum or its heavy fractions originating from refinement, what will provide for increase in yieldings of gas, diesel and other fractions during refinement or cracking. FIG. 8 shows a flow chart showing said alternatives.

The experts in the art will conclude, from the above description, that the process to produce biodiesel and/or fuel oil from algal and/or microbial oil-producing biomass of the present invention is an innovative and ecologically sustainable technology not generating any kind of residue, also providing for the advantage of releasing considerable quantities of oxygen into the atmosphere from the production tanks of algal biomass.

The invention claimed is:

1. A process for producing biodiesel and/or fuel oil, comprising the steps of:
    (a) cultivating oil-producing microbial biomass under conditions sufficient for oil accumulation thereof using residues of sugar cane as a carbon source, wherein the microbe is a yeast or fungus;
    (b) obtaining a liquid effluent resulting from the cultivating of step (a) and in the obtained liquid effluent cultivating oil-producing algal biomass under conditions sufficient for oil accumulation thereof;
    (c) extracting the accumulated oil from the oil-producing microbial biomass and the oil-producing algal biomass using organic solvent or thermopressurized direct liquefaction; and
    (d) reacting the extracted oil with an alcohol to produce the biodiesel and/or fuel oil.

2. The process of claim 1, wherein
    in step a), the oil-producing microbe is *Rhodosporidium toruloides*, and wherein the cultivating results in a residual broth and production of $CO_2$; and
    in step b), the liquid effluent comprises said residual broth, the oil-producing algae is *Botryococcus braunii*, and wherein the cultivating comprises cultivating the algae with the $CO_2$ and the liquid effluent; and
    further comprising:
    prior to step (b) separating the oil-producing microbial biomass from the liquid effluent comprising the residual broth; and
    transesterifying the extracted oils.

3. The process of claim 2, wherein the carbon source further comprises glycerol.

4. The process of claim 2, further comprising the step of preparing an inoculate of the strain *Rhodosporidium toruloides* in solid yeast medium (YM medium), and incubating the inoculate in an oven at 30° C. for five days and incubation for a period of about 72 hours, the YM medium composed per volume thereof of 10 g/l glucose, 5.0 g/l peptone, 3.0 g/l yeast extract, 3.0 g/l malt extract, and 20 g/l agar, and said YM medium having a pH of 5.0.

5. The process of claim 2, wherein the cultivating the oil-producing microbial biomass comprises cultivating in a bioreactor provided with mechanical shaking for a period of 24 hours to 150 hours at a carbon:nitrogen ratio between 0.5 and 500 (w/w), a pH between 2.5 and 8.5, a temperature between 10 and 50° C., and aerating with a volume of air per volume of the biomass per minute (v/v/m) of 0.1 to 5 v/v/m.

6. The process of claim 2, wherein the cultivating the oil-producing microbial biomass comprises the steps of:
    preparing a pre-inoculate medium comprising per volume thereof 10 g/l glucose, 5 g/l peptone, 3 g/l yeast extract, and 3 g/l malt extract;
    preparing an adaptation medium comprising per volume thereof 10 g/l sugar cane molasses, 5 g/l concentrated and detoxified sugar cane bagasse hydrolysate (DHCB), 5 g/l glycerol, and 5 g/l yeast extract; and
    preparing a propagation medium comprising per volume thereof 40 g/l sugar cane molasses, 30 g/l DHCB, 30 g/l glycerol, 5 g/l yeast extract, 2.5 g/l urea, and 0.5 ml/l antifoaming agent,
    wherein all of the prepared media are prepared at a pH of about 5.0.

7. The process of claim 6, wherein the cultivating the algal biomass comprises the steps of:
    adapting the algae in the residual broth in cultures incubating for a period of about fifteen days, during which period the algae is maintained at a temperature of 25±2° C., shaken at about 110 rpm, provided about 1500 Lux of lightning irradiation intensity for twelve-hour periods alternating with twelve hours of darkness, and wherein the algal biomass is formed, filtered, washed with distilled water, and then dried in an oven at about 100° C. for 24 hours;
    preparing an inoculate having about 0.2 g of the adapted algae per liter of the inoculate; and
    activating the inoculate, in a photobioreactors containing the residual broth of the oil-producing microbial biomass, which are provided with: shaking, aerating with a volume of atmospheric air per volume of the biomass per minute (v/v/m) of about 1 v/v/m, maintaining at a temperature between 30±2° C., illuminating with 1500 Lux, and cultivating for a period of time of fifteen days;
    injecting the $CO_2$ from step (a) within photo bioreactors, which by bubbling the $CO_2$ so as to reach a concentration in dissolved form in the medium of about 0.1 to 30% (v/v); and
    separating or harvesting the algal biomass produced, by centrifugation and/or filtering.

8. The process of claim 2, wherein the extracting of the accumulated oil comprises passing the oil-producing microbial biomass and the oil-producing algal biomass through a process of cellular disruption wherein the extracting optionally comprises extracting the accumulated oils through a Soxhlet extractor and/or by a direct thermopressurized liquefaction.

9. The process of claim 2 or 8, wherein the biodiesel is a transesterified biodiesel and wherein the transesterifying produces a residual glycerol which residual glycerol is recirculated to feed into a production bioreactor containing the oil-producing microbial biomass.

10. The process of claim 2 or 8, wherein the biodiesel and/or biooil are produced for direct use as fuels to generate heat and/or steam or as adjuvants to gross petroleum or heavy fractions thereof originating from refinement.

11. The process of claim 1, wherein in the step of cultivating the oil-producing microbial biomass comprises at least one filamentous fungi and/or yeast selected from the group consisting of *Candida curvata, Candida guilhermondi, Candida tropicalis, Candida* sp.*, Candida oleophila, Candida lipolitica, Cryptococcus terricolus, Hansenula saturnus, Hansenula ciferrii, Lipomyces starkeyi, Rhodosporidium toruloides (Rhodotorula gracilis), Aspergillus fischeri, Aspergillus fumigatus, Aspergillus nidulans, Aspergillus ochrceus, Aspergillus terreus, Aspergillus ustus, Cladosporium fulvum, Cladosporium herbarum, Mucor miehei, Penicillium gladioli, Penicillium javanicum, Penicillium lilacinum, Penicillium spinulosum, Penicillium ultimum, Cryptococcus albidus, Rhodotorula glutinis, Trichosporon pullulans, Mortierrella hygrophila, Mortierrella zychae,*

*Mortierrella elongata, Mortierrella parvispora, Mortierrella schmuckeri, Mortierrella alpina, Lypomyces lipofer, Lipomyces tetrasporus, Williopsis saturnus, Candida diddensiae, Yarrowia lipolitica*, and *Trichosporon cutaneum*.

12. The process of claim 1, wherein in the step of cultivating the oil-producing algal biomass comprises an algae and/or cyanobacteriae in an isolated culture or in co-cultures, and said algae and/or cyanobacteriae is selected from the group consisting of *Euglena, Anabaena, Dunaliella, Achananthes, Amphora, Ankistrodesmus, Chaetoceros, Clorococcum, Chlorrella, Chromonas, Chrysosphaera, Cricophaera, Cryptomonas, Cyclotella, Navicula, Amphiprora, Eustigmatophyte, Pleuorochysis, Franceia, Gleocapsa, Gloeothamnion, Hymenomonas, Isochrysis galbana, Monoraphidium, Nannochloropsis, Nephrochloris, Nitzschia, Ochromonas, Oocystis, Oscillatoria, Phaeodactylum, Platymonas, Pleurochrysis, Prymnesiophyte, Pseudoanabaena, Pyraminonas, Stichococcus, Synechococcus, Tetraselmis, Thalassiosira*, and mutant strains having all the identifying characteristics thereof that are able to accumulate lipids in their biomass.

13. The process of claim 12, wherein the algae and/or cyanobacteriae is selected from the group consisting of *Euglena gracilis, Anabaena variabilis, Anabaena cylindrica, Anabaena hassali, Anabaena planctonica, Dunaliella salina, Dunaliella bardawil, Dunaliella tertioleta, Achananthes orientalis, Amphora delicatissima, Amphora cafeiformis, Ankistrodesmus falcatus, Chaetoceros muelleri, Chaetoceros gracilis, Chaetoceros muelleri, Chaetoceros subsalsum, Chlorrella ellipsoidea, Chlorrella salina, Cyclotella meneghiniana, Cyclotella cryptica, Navicula saprophil, Navicula pseudotenelloides, Navicula biskanterae, Navicula acceptata, Navicula saprophila, Navicula pseudotenelloides, Amphiprora hyalina, Eustigmatophyte flagellate, Nannochloropsis salina, Nitzschia pusilla, Nitzschia monoensis, Nitzschia elliptica, Nitzschia alexandrina, Nitzschia quadrangula, Nitzschia inconspicua, Nitzschia microcephala, Nitzschia frustulum, Nitzschia hantzchianna, Nitzschia intermedia, Nitzschia frustulum, Nitzschia communis, Oocystis pusilla, Oscillatoria subborevis, Oscillatoria limnetica, Phaeodactylum tricornutum, Pleurochrysis dentate, Tetraselmis suecica, Thalassiosira weissflogii*, and mutant strains having all the identifying characteristics thereof that are able to accumulate lipids in their biomass.

14. The process of claim 1, wherein the residues of sugar cane are selected from the group consisting of concentrated and detoxified hydrolyzed sugar cane bagasse (DHCB), juice, molasses, brown sugar, and white sugar.

15. The process of claim 14, wherein the residues of sugar cane is sugar cane bagasse that has been subjected to pretreatment, comprising (i) treating the sugar cane bagasse with physical means, physical/chemical means, chemical means, biological means, and combinations thereof, wherein the pretreatment changes the size and structure of lignocellulose fibers, micro and macroscopically and the chemical composition and submicroscopic structure of the sugar cane bagasse before the sugar cane bagasse is hydrolyzed, and then (ii) hydrolyzing the sugar cane bagasse by chemical or enzymatic means.

16. The process of claim 15, wherein the treating (i) of the sugar cane bagasse comprises treating dry sugar cane bagasse particles of 0.1-0.8 mm in diameter, wherein the hydrolyzing (ii) comprises hydrolyzing the sugar cane bagasse at about 125° C. for a period of about twenty minutes, and providing for each 1 kg of dry sugar cane bagasse about 120 grams of concentrated sulfuric acid and in a solid-liquid ratio of 1:10 (w/v) thereby obtaining a hydrolysate, and further comprising concentrating and detoxifying the hydrolysate thereby obtaining said DHCB.

\* \* \* \* \*